(12) United States Patent
Van Der Laan et al.

(10) Patent No.: US 8,323,948 B2
(45) Date of Patent: Dec. 4, 2012

(54) ASPARAGINASES AND USES THEREOF

(75) Inventors: Jan Metske Van Der Laan, Breda (NL); Mark Cristiaan Stor, Gouda (NL); Ilse De Lange, Hellevoetsluis (NL); Lisette Mohrmann, Bergschenhoek (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/137,597

(22) Filed: Aug. 29, 2011

(65) Prior Publication Data

US 2012/0045549 A1 Feb. 23, 2012

Related U.S. Application Data

(63) Continuation of application No. 12/596,705, filed as application No. PCT/EP2008/054693 on Apr. 17, 2008, now abandoned.

(30) Foreign Application Priority Data

| Apr. 20, 2007 | (EP) | ................................ | 07106660 |
| Apr. 20, 2007 | (EP) | ................................ | 07106662 |
| Apr. 20, 2007 | (EP) | ................................ | 07106664 |

(51) Int. Cl.
| C12N 9/00 | (2006.01) |
| C12N 9/78 | (2006.01) |
| C12N 1/20 | (2006.01) |
| C12N 15/00 | (2006.01) |

(52) U.S. Cl. .................... 435/227; 435/183; 435/252.3; 435/320.1; 536/23.2

(58) Field of Classification Search ........................ None
See application file for complete search history.

(56) References Cited

U.S. PATENT DOCUMENTS

| 7,396,670 | B2 | 7/2008 | Budolfsen et al. |
| 7,514,113 | B2 | 4/2009 | Zyzak et al. |
| 7,524,519 | B2 | 4/2009 | Zyzak et al. |
| 2004/0058046 | A1 | 3/2004 | Zyzak et al. |
| 2004/0101607 | A1 | 5/2004 | Zyzak et al. |
| 2005/0202153 | A1 | 9/2005 | Zyzak et al. |
| 2006/0275879 | A1 | 12/2006 | Lynglev et al. |
| 2007/0042080 | A1 | 2/2007 | Plomp et al. |
| 2008/0095883 | A1 | 4/2008 | Budolfsen et al. |
| 2008/0096260 | A1 | 4/2008 | Budolfsen et al. |
| 2009/0191310 | A1 | 7/2009 | Zyzak et al. |

FOREIGN PATENT DOCUMENTS

| EP | 1 704 782 | 9/2006 |
| WO | 2004/026042 | 4/2004 |
| WO | 2004/026043 | 4/2004 |
| WO | 2004/030468 | 4/2004 |
| WO | 2004/032648 | 4/2004 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession A1D4Y2. Jan. 23, 2007.*
International Search Report for PCT/EP2008/054693, mailed Sep. 3, 2008.
Chica et al., Curr. Opin. Biotechnol. Aug. 2005; 16(4):378-84.
Sen et al, Appl. Biochem. Biotechnol. Dec. 2007; 143(3):212-23.
Accession Q4WKE2. Jul. 5, 2005.
English Translation of Office Action issued in corresponding Chilliean Application No. 1128-2008 forwarded on Apr. 19, 2012.
Williams GJ, et al, "Directed evolution of enzymes for biocatalysis and the life sciences". Cell Mol Life Science. Dec. 2004; 61 (24):3034-46.

* cited by examiner

*Primary Examiner* — Christian Fronda
(74) *Attorney, Agent, or Firm* — Baker Donelson Bearman Caldwell & Berkowitz, PC

(57) ABSTRACT

The present invention relates to an asparaginase having the width of the pH activity profile which is at least 3.5. Furthermore the invention relates to newly identified asparaginase polypeptide according to any one of SEQ ID NO: 2 or SEQ ID NO: 4 and to variants thereof and to polynucleotide sequences that encode such novel asparaginase variants. Furthermore the invention relates to the use of these novel asparaginase variants in industrial processes.

14 Claims, 1 Drawing Sheet

```
                    ....|....|  ....|....|  ....|....|  ....|....|  ....|....|
                            10          20          30          40          50
WT A.NIGER          MPLKPILLSA  LASLASASPL  LYSRTTNETF  VFTNANGLNF  TQMNTTLPNV
SEQ ID NO:4         MPLKPILLSA  LASLASASPL  LYSRTTNETF  VFTNSNGLNF  TQMNTTLPNV
SEQ ID NO:2         MPLKPILLSA  LASLASASPL  LYSRATNTTY  VFTNSNGLNF  TQMNTTLPNV

....|....|  ....|....|  ....|....|  ....|....|  ....|....|
                            60          70          80          90         100
WT A.NIGER          TIFATGGTIA  GSDSSSTATT  GYTSGAVGVL  SLIDAVPSML  DVANVAGVQV
SEQ ID NO:4         TILATGGTIA  GSSADNTATT  GYTAGAIGIQ  TLIDAVPEML  DVANVAGVQV
SEQ ID NO:2         TILATGGTIA  GSSADNTATT  GYTAGAIGIQ  TLIDAVPEML  DVANVAGVQV

....|....|  ....|....|  ....|....|  ....|....|  ....|....|
                           110         120         130         140         150
WT A.NIGER          ANVGSEDITS  DILISMSKKL  NRVVCEDPTM  AGAVITHGTD  TLEETAFFLD
SEQ ID NO:4         ANVGSPDVTS  SILLSMAKTL  NEVVCDDPTM  AGAVITHGTD  TLEETAFFLD
SEQ ID NO:2         ANVGSPDVTS  SILLSMAKTL  NEVVCDDPTM  SGAVITHGTD  TLEETAFFLD

....|....|  ....|....|  ....|....|  ....|....|  ....|....|
                           160         170         180         190         200
WT A.NIGER          ATVNCGKPIV  IVGAMRPSTA  ISADGPFNLL  EAVTVAASTS  ARDRGAMVVM
SEQ ID NO:4         ATVNCGKPIV  VVGAMRPATA  ISADGPFNLL  QAVTVAASPA  ARDRGALVVM
SEQ ID NO:2         ATVNCGKPIV  VVGAMRPATA  ISADGPFNLL  QAVTVAASPA  ARDRGALVVM

....|....|  ....|....|  ....|....|  ....|....|  ....|....|
                           210         220         230         240         250
WT A.NIGER          NDRIASAYYV  TKTNANTMDT  FKAMEMGYLG  EMISNTPFFF  YPPVKPTGKV
SEQ ID NO:4         NDRIVSAFYV  SKTNANTMDT  FKAVEMGNLG  AIVSNKPYFF  YPPVKPTGKT
SEQ ID NO:2         NDRIVSAFYA  SKTNANTMDT  FKAVEMGNLG  AIVSNKPYFY  YPPVKPTGKT

....|....|  ....|....|  ....|....|  ....|....|  ....|....|
                           260         270         280         290         300
WT A.NIGER          AFDITNVTEI  PRVDILFSYE  DMHNDTLYNA  ISSGAQGIVI  AGAGAGGVTT
SEQ ID NO:4         TFDVRNVTSI  PRVDILYSYQ  DMHNDTLYDA  IDNGAKGIVI  AGSGAGSVSS
SEQ ID NO:2         TVDVRNVTSI  PRVDILYSYQ  DMQNDTLYSA  IDNGAKGIVI  AGSGAGSVST

....|....|  ....|....|  ....|....|  ....|....|  ....|....|
                           310         320         330         340         350
WT A.NIGER          SFNEAIEDVI  NRLEIPVVQS  MRTVNGEVPL  SDVSSDTATH  IASGYLNPQK
SEQ ID NO:4         GFSDAIEDII  STHSIPIVQS  TRTGNGEVPP  SDESS----Q  IASGFLNPQK
SEQ ID NO:2         GFSDAIDDIA  SKHSIPIVLS  TRTGNGEVPT  SDVSSDTATH  IASGFLNPQK

....|....|  ....|....|  ....|...
                           360         370
WT A.NIGER          SRILLGLLLS  QGKNITEIAD  VFALGTDA
SEQ ID NO:4         SRILLGLLLA  QGKGIEEIRE  VFAKVGVA
SEQ ID NO:2         ARILLGLLLA  EGKGFKEIRE  VFAKVTVA
```

ASPARAGINASES AND USES THEREOF

This application is a continuation of application Ser. No. 12/596,705 filed Oct. 20, 2009 now abandoned which is a 371 of PCT/EP2008/054693 filed Apr. 17, 2008 which designated the U.S. and claims priority to European Application Nos. 07106662.5 filed Apr. 20, 2007, 07106660.9 filed Apr. 20, 2007, and 07106664.1 filed Apr. 20, 2007, the entire contents of each of which are hereby incorporated by reference.

FIELD OF THE INVENTION

The invention relates to newly identified asparaginase polypeptide variants and to polynucleotide sequences comprising genes that encode these novel asparaginases. The invention features the amino acid sequence of the full-length functional protein and functional equivalents of the gene or the amino acid sequence. The invention also relates to methods of using these variant proteins in industrial processes. Also included in the invention are cells transformed with a polynucleotide according to the invention suitable for producing these proteins and cells, wherein a protein according to the invention is genetically modified to enhance or reduce its activity and/or level of expression. The invention also relates to methods of using these proteins in industrial processes.

BACKGROUND OF THE INVENTION

Recently, the occurrence of acrylamide in a number of heated food products was published (Tareke et al. Chem. Res. Toxicol. 13, 517-522 (2000)). Since acrylamide is considered as probably carcinogenic for animals and humans, this finding had resulted in world-wide concern. Further research revealed that considerable amounts of acrylamide are detectable in a variety of baked, fried and oven prepared common foods and it was demonstrated that the occurrence of acrylamide in food was the result of the heating process.

A pathway for the formation of acrylamide from amino acids and reducing sugars as a result of the Maillard reaction has been proposed by Mottram et al. Nature 419:448 (2002). According to this hypothesis, acrylamide may be formed during the Maillard reaction. During baking and roasting, the Maillard reaction is mainly responsible for the color, smell and taste. A reaction associated with the Maillard is the Strecker degradation of amino acids and a pathway to acrylamide was proposed. The formation of acrylamide became detectable when the temperature exceeded 120° C., and the highest formation rate was observed at around 170° C. When asparagine and glucose were present, the highest levels of acrylamide could be observed, while glutamine and aspartic acid only resulted in trace quantities.

The official migration limit in the EU for acrylamide migrating into food from food contact plastics is set at 10 ppb (10 micrograms per kilogram). Although no official limit is yet set for acrylamide that forms during cooking, the fact that a lot of products exceed this value, especially cereals, bread products and potato or corn based products, causes concern.

Several plant raw materials are known to contain substantial levels of asparagine. In potatoes asparagine is the dominant free amino acid (940 mg/kg, corresponding with 40% of the total amino-acid content) and in wheat flour asparagine is present as a level of about 167 mg/kg, corresponding with 14% of the total free amino acids pool (Belitz and Grosch in Food Chemistry—Springer N.Y., 1999). The fact that acrylamide is formed mainly from asparagine (combined with reducing sugars) may explain the high levels acrylamide in fried, oven-cooked or roasted plant products. Therefore, in the interest of public health, there is an urgent need for food products that have substantially lower levels of acrylamide or, preferably, are devoid of it.

A variety of solutions to decrease the acrylamide content has been proposed, either by altering processing variables, e.g. temperature or duration of the heating step, or by chemically or enzymatically preventing the formation of acrylamide or by removing formed acrylamide.

In several patent applications the use of asparaginase for decreasing the level of asparagine and thereby the amount of acrylamide formed has been disclosed. Suitable asparaginases for this purpose have been yielded from several fungal sources, as for example *Aspergillus niger* in WO2004/030468 and *Aspergillus oryzae* in WO04/032648.

Although all L-asparaginases catalyze the same chemical conversion, this does not mean that they are suitable for the same applications. Various applications will place different demands on the conditions under which the enzymes have to operate. Physical and chemical parameters that may influence the rate of an enzymatic conversion are the temperature (which has a positive effect on the chemical reaction rates, but may have a negative effect on enzyme stability), the moisture content, the pH, the salt concentration, the structural integrity of the food matrix, the presence of activators or inhibitors of the enzyme, the concentration of the substrate and products, etc.

Therefore there exists an ongoing need for improved asparaginases for several applications having improved properties.

OBJECT OF THE INVENTION

It is an object of the invention to provide novel asparaginase variant polypeptides and polynucleotides encoding such variants. A further object is to provide recombinant strains producing such asparaginase variants. Also fusion polypeptides are part of the invention, as well as methods of making and using the polynucleotides and polypeptides according to the invention.

SUMMARY OF THE INVENTION

The invention provides for novel polypeptide variants having asparaginase activity. In particular, the invention provides a variant asparaginase having the amino acid sequence set out in any one of SEQ ID NO: 2 or SEQ ID NO: 4, and further variants thereof having at least 85% homology to at least one of them. Typically, such further variants of the invention will be functional equivalents of the polypeptide of any one of SEQ ID NO: 2 or SEQ ID NO: 4. The term 'functional equivalent' is herein intended to require that such functional equivalent polypeptides at least have to have asparaginase activity.

The present invention also provides an asparaginase having the width of the pH activity profile which is at least 3.5, preferably at least 4, more preferably at least 5 pH units wide. In the context of the present invention the width of the pH activity profile is the width of the pH range (calculated in pH units) where the enzyme exhibits 50 to 100% of its maximal activity. The width of the pH activity profile of the enzyme can be calculated as indicated in the examples. The asparaginase having the width of the pH activity profile which is at least 3.5 can either be isolated from natural sources or it can be an artificial asparaginase enzyme. In a preferred embodiment the asparaginase having the width of the pH activity profile which is at least 3.5, preferably at least 4, more preferably at least 5 pH units wide, is an asparaginase according to a variant asparaginase having the amino acid sequence set out in any one of SEQ ID NO: 2 or SEQ ID NO: 4, and further variants thereof having at least 85% homology to at least one of them.

In one embodiment of the invention, the invention provides for an isolated polynucleotide comprising a nucleic acid sequence encoding a polypeptide with an amino acid sequence as shown in SEQ ID NO: 2 or SEQ ID NO: 4 or a variant, for example a functional equivalent, of any of them.

In a further embodiment, the invention provides an isolated polynucleotide encoding at least one functional domain of a polypeptide according to any one of SEQ ID NO: 2 or SEQ ID NO: 4 or a variant, for example a functional equivalent, of any of them.

Furthermore, the invention provides novel polynucleotides that encode for the novel polypeptide variants according to the invention. Furthermore the invention provides a nucleic acid sequence coding for the asparaginase having the width of the pH activity profile which is at least 3.5, preferably at least 4, more preferably at least 5 pH units wide.

The invention also relates to vectors comprising a polynucleotide sequence according to the invention and primers, probes and fragments that may be used to amplify or detect such a polynucleotide according to the invention.

In a further preferred embodiment, a vector is provided wherein a polynucleotide sequence according to the invention is functionally linked with at least one regulatory sequence suitable for expression of the encoded amino acid sequence in a suitable host cell, such as a filamentous fungus, for example *Aspergillus*. The invention also provides methods for preparing polynucleotides and vectors according to the invention.

The invention also relates to recombinantly produced host cells that contain variant (heterologous) polynucleotides according to the invention.

In another embodiment, the invention provides recombinant host cells wherein the expression of a variant asparaginase according to the invention is significantly increased or wherein the activity of the produced asparaginase is increased.

In another embodiment, the invention provides for a recombinantly produced host cell that contains a polynucleotide according to the invention and, accordingly, wherein the cell is capable of producing a functional variant asparaginase according to the invention, preferably a cell capable of overexpressing the variant asparaginase according to the invention, for example an *Aspergillus niger* strain comprising a polynucleotide according to the invention.

In yet another aspect of the invention, a purified variant polypeptide is provided. The polypeptides according to the invention include the polypeptides encoded by the polynucleotides according to the invention. Especially preferred is a variant polypeptide according to any one of SEQ ID NO: 2 or SEQ ID NO: 4 or a variant, for example a functional equivalent, of any of them.

Fusion proteins comprising a polypeptide according to the invention are also within the scope of the invention.

The invention also provides methods of making the variant polypeptides according to the invention.

The invention also relates to the use of the variant asparaginase according to the invention in any industrial process as described herein.

DESCRIPTION OF THE FIGURE

FIG. 1. Alignment of SEQ ID NO: 2 and SEQ ID NO: 4 with the *A. niger* wild type Asparaginase as disclosed in SEQ ID NO: 3 of WO2004/030468.

DETAILED DESCRIPTION OF THE INVENTION

Throughout the present specification and accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The present invention relates to a variant asparaginase sequence having the sequence set out in any one of SEQ ID NO: 2 or SEQ ID NO: 4 and to further variants thereof.

Hereunder for both polypeptide sequences specifics are set out.

The sequence of SEQ ID NO: 2 comprises the following substitutions as compared with a wild-type asparaginase sequence obtained from *Aspergillus niger* as disclosed in WO 2004/030468: T25A, E28T, F30Y, A35S, F53L, D63S, S64A, S65D, S66N, S74A, V77I, V79I, L80Q, S81T, S88E, E106P, I108V, D111S, I114L, S117A, K119T, R122E, E126D, A131S, I161V, S168A, E181Q, T189P, S190A, M197L, A205V, Y208F, V210A, T211S, M224V, Y228N, E231A, M232I, I233V, T236K, F238Y, F240Y, V250T, A251T, F252V, I254V, T255R, E259S, F267Y, E270Q, H273Q, N279S, S282D, S283N, Q286K, A293S, G297S, T299S, S301G, N303S, E304D, E307D, V309I, I310A, N311S, R312K, L313H, E314S, V317I, Q319L, M321T, V324G, L330T, Y345F, S351A, S360A, Q361E, N364G, I365F, T366K, A369R, D370E, L374K, G375V and D377V.

The wild-type asparaginase sequence obtained from *A. niger* as disclosed in WO 2004/030468 is disclosed therein as SEQ ID NO: 3 (amino acid sequence). The asparaginase set out in SEQ ID NO: 2 of the instant application is tentatively called ASN001.

A variant of the sequence set out in SEQ ID NO: 2, for example a functional equivalent, may comprise one or more of Ala at position 25, Thr at position 28, Tyr at position 30, Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Ser at position 131, Val at position 161, Ala at position 168, Gln at position 181, Pro at position 189, Ala at position 190, Leu at position 197, Val at position 205, Phe at position 208, Ala at position 210, Ser at position 211, Val at position 224, Asn at position 228, Ala at position 231, Ile at position 232, Val at position 233, Lys at position 236, Tyr at position 238, Tyr at position 240, Thr at position 250, Thr at position 251, Val at position 252, Val at position 254, Arg at position 255, Ser at position 259, Tyr at position 267, Gln at position 270, Gln at position 273, Ser at position 279, Asp at position 282, Asn at position 283, Lys at position 286, Ser at position 293, Ser at position 297, Ser at position 299, Gly at position 301, Ser at position 303, Asp at position 304, Asp at 307, Ile at position 309, Ala at position 310, Ser at position 311, Lys at position 312, His at position 313, Ser at position 314, Ile at position 317, Leu at position 319, Thr at position 321, Gly at position 324, Thr at position 330, Phe at position 345, Ala at position 351, Ala at position 360, Glu at position 361, Gly at position 364, Phe at position 365, Lys at position 366, Arg at position 369, Glu at position 370, Lys at position 374, Val at position 375 or Val at position 377, said positions being defined with reference to SEQ ID NO: 2.

That is to say, when a variant of the sequence set out in SEQ ID NO: 2 is aligned with the sequence set out in SEQ ID NO: 2, the variant may comprise one or more of:

Ala at the position (in the variant) corresponding to position 25 in SEQ ID NO: 2;
Thr at the position (in the variant) corresponding to position 28 in SEQ ID NO: 2;
Tyr at the position (in the variant) corresponding to position 30 in SEQ ID NO: 2;
Ser at the position (in the variant) corresponding to position 35 in SEQ ID NO: 2;
Leu at the position (in the variant) corresponding to position 53 in SEQ ID NO: 2;
Ser at the position (in the variant) corresponding to position 63 in SEQ ID NO: 2;
Ala at the position (in the variant) corresponding to position 64 in SEQ ID NO: 2;
Asp at the position (in the variant) corresponding to position 65 in SEQ ID NO: 2;
Asn at the position (in the variant) corresponding to position 66 in SEQ ID NO: 2;
Ala at the position (in the variant) corresponding to position 74 in SEQ ID NO: 2;
Ile at the position (in the variant) corresponding to position 77 in SEQ ID NO: 2;
Ile at the position (in the variant) corresponding to position 79 in SEQ ID NO: 2;
Gln at the position (in the variant) corresponding to position 80 in SEQ ID NO: 2;
Thr at the position (in the variant) corresponding to position 81 in SEQ ID NO: 2;
Glu at the position (in the variant) corresponding to position 88 in SEQ ID NO: 2;
Pro at the position (in the variant) corresponding to position 106 in SEQ ID NO: 2;
Val at the position (in the variant) corresponding to position 108 in SEQ ID NO: 2;
Ser at the position (in the variant) corresponding to position 111 in SEQ ID NO: 2;
Leu at the position (in the variant) corresponding to position 114 in SEQ ID NO: 2;
Ala at the position (in the variant) corresponding to position 117 in SEQ ID NO: 2;
Thr at the position (in the variant) corresponding to position 119 in SEQ ID NO: 2;
Glu at the position (in the variant) corresponding to position 122 in SEQ ID NO: 2;
Asp at the position (in the variant) corresponding to position 126 in SEQ ID NO: 2;
Ser at the position (in the variant) corresponding to position 131 in SEQ ID NO: 2;
Val at the position (in the variant) corresponding to position 161 in SEQ ID NO: 2;
Ala at the position (in the variant) corresponding to position 168 in SEQ ID NO: 2;
Gln at the position (in the variant) corresponding to position 181 in SEQ ID NO: 2;
Pro at the position (in the variant) corresponding to position 189 in SEQ ID NO: 2;
Ala at the position (in the variant) corresponding to position 190 in SEQ ID NO: 2;
Leu at the position (in the variant) corresponding to position 197 in SEQ ID NO: 2;
Val at the position (in the variant) corresponding to position 205 in SEQ ID NO: 2;
Phe at the position (in the variant) corresponding to position 208 in SEQ ID NO: 2;
Ala at the position (in the variant) corresponding to position 210 in SEQ ID NO: 2;
Ser at the position (in the variant) corresponding to position 211 in SEQ ID NO: 2;
Val at the position (in the variant) corresponding to position 224 in SEQ ID NO: 2;
Asn at the position (in the variant) corresponding to position 228 in SEQ ID NO: 2;
Ala at the position (in the variant) corresponding to position 231 in SEQ ID NO: 2;
Ile at the position (in the variant) corresponding to position 232 in SEQ ID NO: 2;
Val at the position (in the variant) corresponding to position 233 in SEQ ID NO: 2;
Lys at the position (in the variant) corresponding to position 236 in SEQ ID NO: 2;
Tyr at the position (in the variant) corresponding to position 238 in SEQ ID NO: 2;
Tyr at the position (in the variant) corresponding to position 240 in SEQ ID NO: 2;
Thr at the position (in the variant) corresponding to position 250 in SEQ ID NO: 2;
Thr at the position (in the variant) corresponding to position 251 in SEQ ID NO: 2;
Thr at the position (in the variant) corresponding to position 252 in SEQ ID NO: 2;
Val at the position (in the variant) corresponding to position 254 in SEQ ID NO: 2;
Arg at the position (in the variant) corresponding to position 255 in SEQ ID NO: 2;
Ser at the position (in the variant) corresponding to position 259 in SEQ ID NO: 2;
Tyr at the position (in the variant) corresponding to position 267 in SEQ ID NO: 2;
Gln at the position (in the variant) corresponding to position 270 in SEQ ID NO: 2;
Gln at the position (in the variant) corresponding to position 273 in SEQ ID NO: 2;
Asp at the position (in the variant) corresponding to position 279 in SEQ ID NO: 2;
Asp at the position (in the variant) corresponding to position 282 in SEQ ID NO: 2;
Asn at the position (in the variant) corresponding to position 283 in SEQ ID NO: 2;
Lys at the position (in the variant) corresponding to position 286 in SEQ ID NO: 2;
Ser at the position (in the variant) corresponding to position 293 in SEQ ID NO: 2;
Ser at the position (in the variant) corresponding to position 297 in SEQ ID NO: 2;
Ser at the position (in the variant) corresponding to position 299 in SEQ ID NO: 2;
Gly at the position (in the variant) corresponding to position 301 in SEQ ID NO: 2;
Ser at the position (in the variant) corresponding to position 303 in SEQ ID NO: 2;
Asp at the position (in the variant) corresponding to position 304 in SEQ ID NO: 2;
Asp at the position (in the variant) corresponding to position 307 in SEQ ID NO: 2;
Ile at the position (in the variant) corresponding to position 309 in SEQ ID NO: 2;

Ala at the position (in the variant) corresponding to position 310 in SEQ ID NO: 2;
Ser at the position (in the variant) corresponding to position 311 in SEQ ID NO: 2;
Thr at the position (in the variant) corresponding to position 312 in SEQ ID NO: 2;
His at the position (in the variant) corresponding to position 313 in SEQ ID NO: 2;
Ser at the position (in the variant) corresponding to position 314 in SEQ ID NO: 2;
Ile at the position (in the variant) corresponding to position 317 in SEQ ID NO: 2;
Leu at the position (in the variant) corresponding to position 319 in SEQ ID NO: 2;
Thr at the position (in the variant) corresponding to position 321 in SEQ ID NO: 2;
Gly at the position (in the variant) corresponding to position 324 in SEQ ID NO: 2;
Pro at the position (in the variant) corresponding to position 330 in SEQ ID NO: 2;
Phe at the position (in the variant) corresponding to position 345 in SEQ ID NO: 2;
Ala at the position (in the variant) corresponding to position 351 in SEQ ID NO: 2;
Ala at the position (in the variant) corresponding to position 360 in SEQ ID NO: 2;
Glu at the position (in the variant) corresponding to position 361 in SEQ ID NO: 2;
Gly at the position (in the variant) corresponding to position 364 in SEQ ID NO: 2;
Phe at the position (in the variant) corresponding to position 365 in SEQ ID NO: 2;
Lys at the position (in the variant) corresponding to position 366 in SEQ ID NO: 2;
Arg at the position (in the variant) corresponding to position 369 in SEQ ID NO: 2;
Glu at the position (in the variant) corresponding to position 370 in SEQ ID NO: 2;
Lys at the position (in the variant) corresponding to position 374 in SEQ ID NO: 2;
Val at the position (in the variant) corresponding to position 375 in SEQ ID NO: 2; or
Val at the position (in the variant) corresponding to position 377 in SEQ ID NO: 2;

A variant asparaginase polypeptide of the invention may comprise two, three, four, five, for example at least 10, at least 15, at least 20, such as at least 25, at least 30, at least 40, at least 50, at least 60, at least 70, at least 80 or all of the following amino acids: Ala at position 25, Thr at position 28, Tyr at position 30, Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Ser at position 131, Val at position 161, Ala at position 168, Gln at position 181, Pro at position 189, Ala at position 190, Leu at position 197, Val at position 205, Phe at position 208, Ala at position 210, Ser at position 211, Val at position 224, Asn at position 228, Ala at position 231, Ile at position 232, Val at position 233, Lys at position 236, Tyr at position 238, Tyr at position 240, Thr at position 250, Thr at position 251, Val at position 252, Val at position 254, Arg at position 255, Ser at position 259, Tyr at position 267, Gln at position 270, Gln at position 273, Ser at position 279, Asp at position 282, Asn at position 283, Lys at position 286, Ser at position 293, Ser at position 297, Ser at position 299, Gly at position 301, Ser at position 303, Asp at position 304, Asp at 307, Ile at position 309, Ala at position 310, Ser at position 311, Lys at position 312, His at position 313, Ser at position 314, Ile at position 317, Leu at position 319, Thr at position 321, Gly at position 324, Thr at position 330, Phe at position 345, Ala at position 351, Ala at position 360, Glu at position 361, Gly at position 364, Phe at position 365, Lys at position 366, Arg at position 369, Glu at position 370, Lys at position 374, Val at position 375 or Val at position 377, said positions being defined with reference to SEQ ID NO: 2.

Accordingly, a variant asparaginase polypeptide of the invention may comprise any combination of two of more of Ala at position 25, Thr at position 28, Tyr at position 30, Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Ser at position 131, Val at position 161, Ala at position 168, Gln at position 181, Pro at position 189, Ala at position 190, Leu at position 197, Val at position 205, Phe at position 208, Ala at position 210, Ser at position 211, Val at position 224, Asn at position 228, Ala at position 231, Ile at position 232, Val at position 233, Lys at position 236, Tyr at position 238, Tyr at position 240, Thr at position 250, Thr at position 251, Val at position 252, Val at position 254, Arg at position 255, Ser at position 259, Tyr at position 267, Gln at position 270, Gln at position 273, Ser at position 279, Asp at position 282, Asn at position 283, Lys at position 286, Ser at position 293, Ser at position 297, Ser at position 299, Gly at position 301, Ser at position 303, Asp at position 304, Asp at 307, Ile at position 309, Ala at position 310, Ser at position 311, Lys at position 312, His at position 313, Ser at position 314, Ile at position 317, Leu at position 319, Thr at position 321, Gly at position 324, Thr at position 330, Phe at position 345, Ala at position 351, Ala at position 360, Glu at position 361, Gly at position 364, Phe at position 365, Lys at position 366, Arg at position 369, Glu at position 370, Lys at position 374, Val at position 375 or Val at position 377, said positions being defined with reference to SEQ ID NO: 2.

Preferably, a variant asparaginase polypeptide of the invention may comprise all of Ala at position 25, Thr at position 28, Tyr at position 30, Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Ser at position 131, Val at position 161, Ala at position 168, Gln at position 181, Pro at position 189, Ala at position 190, Leu at position 197, Val at position 205, Phe at position 208, Ala at position 210, Ser at position 211, Val at position 224, Asn at position 228, Ala at position 231, Ile at position 232, Val at position 233, Lys at position 236, Tyr at position 238, Tyr at position 240, Thr at position 250, Thr at position 251, Val at position 252, Val at position 254, Arg at position 255, Ser at position 259, Tyr at position 267, Gln at position 270, Gln at position 273, Ser at position 279, Asp at position 282, Asn at position 283, Lys at position 286, Ser at position 293, Ser at position 297, Ser at position 299, Gly at position 301, Ser at position 303, Asp at position 304, Asp at 307, Ile at position 309, Ala at position 310, Ser at position 311, Lys at position 312, His at position 313, Ser at position 314, Ile at position 317, Leu at position 319, Thr at position 321, Gly at position 324, Thr at position 330, Phe at position 345, Ala at position 351, Ala at position 360, Glu at position 361, Gly at position 364, Phe at position 365, Lys at position 366, Arg at position 369, Glu at position 370, Lys at position 374, Val at position 375 or Val at position 377, said positions being defined with reference to SEQ ID NO: 2.

Those positions in a variant asparaginase polypeptide of the invention which correspond to positions 25, 28, 30, 35, 53, 63, 64, 65, 66, 74, 77, 79, 80, 81, 88, 106, 108, 111, 114, 117, 119, 122, 126, 131, 161, 168, 181, 189, 190, 197, 205, 208, 210, 211, 224, 228, 231, 232, 233, 236, 238, 240, 250, 251, 252, 254, 255, 259, 267, 270, 273, 279, 282, 283, 286, 293, 297, 299, 301, 303, 304, 307, 309, 310, 311, 312, 313, 314, 317, 319, 321, 324, 330, 345, 351, 360, 361, 364, 365, 366, 369, 370, 374, 375 and 377 may be identified by aligning the sequence of the variant polypeptide with that of SEQ ID NO: 2 using, for example, the GAP alignment to the most homologous sequence found by the GAP program (see below for details of this program). The positions in the variant corresponding to positions 25, 28, 30, 35, 53, 63, 64, 65, 66, 74, 77, 79, 80, 81, 88, 106, 108, 111, 114, 117, 119, 122, 126, 131, 161, 168, 181, 189, 190, 197, 205, 208, 210, 211, 224, 228, 231, 232, 233, 236, 238, 240, 250, 251, 252, 254, 255, 259, 267, 270, 273, 279, 282, 283, 286, 293, 297, 299, 301, 303, 304, 307, 309, 310, 311, 312, 313, 314, 317, 319, 321, 324, 330, 345, 351, 360, 361, 364, 365, 366, 369, 370, 374, 375 and 377 in SEQ ID NO: 2 may thus be identified and are referred to as those positions defined with reference to SEQ ID NO: 2.

The sequence of SEQ ID NO: 4 comprises the following substitutions as compared with a wild-type asparaginase sequence obtained from *Aspergillus niger* as disclosed in WO 2004/030468: A35S, F53L, D63S, S64A, S65D, S66N, S74A, V77I, V79I, L80O, S81T, S88E, E106P, I108V, D111S, I114L, S117A, K119T, R122E, E126D, I161V, S168A, E181Q, T189P, S190A, M197L, A205V, Y208F, T211S, M224V, Y228N, E231A, M232I, I233V, T236K, F238Y, V250T, A251T, I254V, T255R, E259S, F267Y, E270Q, N279D, S282D, S283N, Q286K, A293S, G297S, T299S, T300S, S301G, N303S, E304D, V309I, N311S, R312T, L313H, E314S, V317I, M321T, V324G, L330P, V333E, H340Q, Y345F, S360A, N364G, T366E, A369R, D370E, L374K, G375V, T376G and D377V.

In addition, the sequence of SEQ ID NO: 4 comprises a four amino acid deletion in comparison with the wild-type asparaginase sequence obtained from *Aspergillus niger* as disclosed in WO 2004/030468, i.e. SEQ ID NO: 4 disclosed herein does not comprise amino acids corresponding to D336, T337, A338 and T339 in the wild-type asparaginase sequence obtained from *Aspergillus niger* as disclosed in WO 2004/030468 and referred to therein as SEQ ID NO: 3 (amino acid sequence). The asparaginase set out in SEQ ID NO: 4 of the instant application is tentatively called ASN002.

A variant of the sequence set out in SEQ ID NO: 4, for example a functional equivalent, may comprise one or more of Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Val at position 161, Ala at position 168, Gln at position 181, Pro at position 189, Ala at position 190, Leu at position 197, Val at position 205, Phe at position 208, Ser at position 211, Val at position 224, Asn at position 228, Ala at position 231, Ile at position 232, Val at position 233, Lys at position 236, Tyr at position 238, Thr at position 250, Thr at position 251, Val at position 254, Arg at position 255, Ser at position 259, Tyr at position 267, Gln at position 270, Asp at position 279, Asp at position 282, Asn at position 283, Lys at position 286, Ser at position 293, Ser at position 297, Ser at position 299, Ser at position 300, Gly at position 301, Ser at position 303, Asp at position 304, Ile at position 309, Ser at position 311, Thr at position 312, His at position 313, Ser at position 314, Ile at position 317, Thr at position 321, Gly at position 324, Pro at position 330, Glu at position 333, Gln at position 336, Phe at position 341, Ala at position 356, Gly at position 360, Glu at position 362, Arg at position 365, Glu at position 366, Lys at position 370, Val at position 371, Gly at position 372 or Val at position 373, said positions being defined with reference to SEQ ID NO: 4.

That is to say, when a variant of the sequence set out in SEQ ID NO: 4 is aligned with the sequence set out in SEQ ID NO: 4, the variant may comprise one of more of:

Ser at the position (in the variant) corresponding to position 35 in SEQ ID NO: 4;
Leu at the position (in the variant) corresponding to position 53 in SEQ ID NO: 4;
Ser at the position (in the variant) corresponding to position 63 in SEQ ID NO: 4;
Ala at the position (in the variant) corresponding to position 64 in SEQ ID NO: 4;
Asp at the position (in the variant) corresponding to position 65 in SEQ ID NO: 4;
Asn at the position (in the variant) corresponding to position 66 in SEQ ID NO: 4;
Ala at the position (in the variant) corresponding to position 74 in SEQ ID NO: 4;
Ile at the position (in the variant) corresponding to position 77 in SEQ ID NO: 4;
Ile at the position (in the variant) corresponding to position 79 in SEQ ID NO: 4;
Gln at the position (in the variant) corresponding to position 80 in SEQ ID NO: 4;
Thr at the position (in the variant) corresponding to position 81 in SEQ ID NO: 4;
Glu at the position (in the variant) corresponding to position 88 in SEQ ID NO: 4;
Pro at the position (in the variant) corresponding to position 106 in SEQ ID NO: 4;
Val at the position (in the variant) corresponding to position 108 in SEQ ID NO: 4;
Ser at the position (in the variant) corresponding to position 111 in SEQ ID NO: 4;
Leu at the position (in the variant) corresponding to position 114 in SEQ ID NO: 4;
Ala at the position (in the variant) corresponding to position 117 in SEQ ID NO: 4;
Thr at the position (in the variant) corresponding to position 119 in SEQ ID NO: 4;
Glu at the position (in the variant) corresponding to position 122 in SEQ ID NO: 4;
Asp at the position (in the variant) corresponding to position 126 in SEQ ID NO: 4;
Val at the position (in the variant) corresponding to position 161 in SEQ ID NO: 4;
Ala at the position (in the variant) corresponding to position 168 in SEQ ID NO: 4;
Gln at the position (in the variant) corresponding to position 181 in SEQ ID NO: 4;
Pro at the position (in the variant) corresponding to position 189 in SEQ ID NO: 4;
Ala at the position (in the variant) corresponding to position 190 in SEQ ID NO: 4;

Leu at the position (in the variant) corresponding to position 197 in SEQ ID NO: 4;
Val at the position (in the variant) corresponding to position 205 in SEQ ID NO: 4;
Phe at the position (in the variant) corresponding to position 208 in SEQ ID NO: 4;
Ser at the position (in the variant) corresponding to position 211 in SEQ ID NO: 4;
Val at the position (in the variant) corresponding to position 224 in SEQ ID NO: 4;
Asn at the position (in the variant) corresponding to position 228 in SEQ ID NO: 4;
Ala at the position (in the variant) corresponding to position 231 in SEQ ID NO: 4;
Ile at the position (in the variant) corresponding to position 232 in SEQ ID NO: 4;
Val at the position (in the variant) corresponding to position 233 in SEQ ID NO: 4;
Lys at the position (in the variant) corresponding to position 236 in SEQ ID NO: 4;
Tyr at the position (in the variant) corresponding to position 238 in SEQ ID NO: 4;
Thr at the position (in the variant) corresponding to position 250 in SEQ ID NO: 4;
Thr at the position (in the variant) corresponding to position 251 in SEQ ID NO: 4;
Val at the position (in the variant) corresponding to position 254 in SEQ ID NO: 4;
Arg at the position (in the variant) corresponding to position 255 in SEQ ID NO: 4;
Ser at the position (in the variant) corresponding to position 259 in SEQ ID NO: 4;
Tyr at the position (in the variant) corresponding to position 267 in SEQ ID NO: 4;
Gln at the position (in the variant) corresponding to position 270 in SEQ ID NO: 4;
Asp at the position (in the variant) corresponding to position 279 in SEQ ID NO: 4;
Asp at the position (in the variant) corresponding to position 282 in SEQ ID NO: 4;
Asn at the position (in the variant) corresponding to position 283 in SEQ ID NO: 4;
Lys at the position (in the variant) corresponding to position 286 in SEQ ID NO: 4;
Ser at the position (in the variant) corresponding to position 293 in SEQ ID NO: 4;
Ser at the position (in the variant) corresponding to position 297 in SEQ ID NO: 4;
Ser at the position (in the variant) corresponding to position 299 in SEQ ID NO: 4;
Ser at the position (in the variant) corresponding to position 300 in SEQ ID NO: 4;
Gly at the position (in the variant) corresponding to position 301 in SEQ ID NO: 4;
Ser at the position (in the variant) corresponding to position 303 in SEQ ID NO: 4;
Asp at the position (in the variant) corresponding to position 304 in SEQ ID NO: 4;
Ile at the position (in the variant) corresponding to position 309 in SEQ ID NO: 4;
Ser at the position (in the variant) corresponding to position 311 in SEQ ID NO: 4;
Thr at the position (in the variant) corresponding to position 312 in SEQ ID NO: 4;
His at the position (in the variant) corresponding to position 313 in SEQ ID NO: 4;
Ser at the position (in the variant) corresponding to position 314 in SEQ ID NO: 4;
Ile at the position (in the variant) corresponding to position 317 in SEQ ID NO: 4;
Thr at the position (in the variant) corresponding to position 321 in SEQ ID NO: 4;
Gly at the position (in the variant) corresponding to position 324 in SEQ ID NO: 4;
Pro at the position (in the variant) corresponding to position 330 in SEQ ID NO: 4;
Glu at the position (in the variant) corresponding to position 333 in SEQ ID NO: 4;
Gln at the position (in the variant) corresponding to position 336 in SEQ ID NO: 4;
Phe at the position (in the variant) corresponding to position 341 in SEQ ID NO: 4;
Ala at the position (in the variant) corresponding to position 356 in SEQ ID NO: 4;
Gly at the position (in the variant) corresponding to position 360 in SEQ ID NO: 4;
Glu at the position (in the variant) corresponding to position 362 in SEQ ID NO: 4;
Arg at the position (in the variant) corresponding to position 365 in SEQ ID NO: 4;
Glu at the position (in the variant) corresponding to position 366 in SEQ ID NO: 4;
Lys at the position (in the variant) corresponding to position 370 in SEQ ID NO: 4;
Val at the position (in the variant) corresponding to position 371 in SEQ ID NO: 4;
Gly at the position (in the variant) corresponding to position 372 in SEQ ID NO: 4; or
Val at the position (in the variant) corresponding to position 373 in SEQ ID NO: 4.

A variant asparaginase polypeptide of the invention may comprise two, three, four, five, for example at least 10, at least 15, at least 20, such as at least 25, at least 30, at least 40, at least 50, at least 60, at least 70 or all of the following amino acids: Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Val at position 161, Ala at position 168, Gln at position 181, Pro at position 189, Ala at position 190, Leu at position 197, Val at position 205, Phe at position 208, Ser at position 211, Val at position 224, Asn at position 228, Ala at position 231, Ile at position 232, Val at position 233, Lys at position 236, Tyr at position 238, Thr at position 250, Thr at position 251, Val at position 254, Arg at position 255, Ser at position 259, Tyr at position 267, Gln at position 270, Asp at position 279, Asp at position 282, Asn at position 283, Lys at position 286, Ser at position 293, Ser at position 297, Ser at position 299, Ser at position 300, Gly at position 301, Ser at position 303, Asp at position 304, Ile at position 309, Ser at position 311, Thr at position 312, His at position 313, Ser at position 314, Ile at position 317, Thr at position 321, Gly at position 324, Pro at position 330, Glu at position 333, Gln at position 336, Phe at position 341, Ala at position 356, Gly at position 360, Glu at position 362, Arg at position 365, Glu at position 366, Lys at position 370, Val at position 371, Gly at position 372 or Val at position 373, said positions being defined with reference to SEQ ID NO: 4.

Accordingly, a variant asparaginase polypeptide of the invention may comprise any combination of two of more of Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Val at position 161, Ala at position 168, Gln at position 181, Pro at position 189, Ala at position 190, Leu at position 197, Val at position 205, Phe at position 208, Ser at position 211, Val at position 224, Asn at position 228, Ala at position 231, Ile at position 232, Val at position 233, Lys at position 236, Tyr at position 238, Thr at position 250, Thr at position 251, Val at position 254, Arg at position 255, Ser at position 259, Tyr at position 267, Gln at position 270, Asp at position 279, Asp at position 282, Asn at position 283, Lys at position 286, Ser at position 293, Ser at position 297, Ser at position 299, Ser at position 300, Gly at position 301, Ser at position 303, Asp at position 304, Ile at position 309, Ser at position 311, Thr at position 312, His at position 313, Ser at position 314, Ile at position 317, Thr at position 321, Gly at position 324, Pro at position 330, Glu at position 333, Gln at position 336, Phe at position 341, Ala at position 356, Gly at position 360, Glu at position 362, Arg at position 365, Glu at position 366, Lys at position 370, Val at position 371, Gly at position 372 or Val at position 373, said positions being defined with reference to SEQ ID NO: 4.

Preferably, a variant asparaginase polypeptide of the invention may comprise all of Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Val at position 161, Ala at position 168, Gln at position 181, Pro at position 189, Ala at position 190, Leu at position 197, Val at position 205, Phe at position 208, Ser at position 211, Val at position 224, Asn at position 228, Ala at position 231, Ile at position 232, Val at position 233, Lys at position 236, Tyr at position 238, Thr at position 250, Thr at position 251, Val at position 254, Arg at position 255, Ser at position 259, Tyr at position 267, Gln at position 270, Asp at position 279, Asp at position 282, Asn at position 283, Lys at position 286, Ser at position 293, Ser at position 297, Ser at position 299, Ser at position 300, Gly at position 301, Ser at position 303, Asp at position 304, Ile at position 309, Ser at position 311, Thr at position 312, His at position 313, Ser at position 314, Ile at position 317, Thr at position 321, Gly at position 324, Pro at position 330, Glu at position 333, Gln at position 336, Phe at position 341, Ala at position 356, Gly at position 360, Glu at position 362, Arg at position 365, Glu at position 366, Lys at position 370, Val at position 371, Gly at position 372 and Val at position 373, said positions being defined with reference to SEQ ID NO: 4.

Those positions in a variant asparaginase polypeptide of the invention which correspond to positions 35, 53, 63, 64, 65, 66, 74, 77, 79, 80, 81, 88, 106, 108, 111, 114, 117, 119, 122, 126, 161, 168, 181, 189, 190, 197, 205, 208, 211, 224, 228, 231, 232, 233, 236, 238, 250, 251, 254, 255, 259, 267, 270, 279, 282, 283, 286, 293, 297, 299, 300, 301, 303, 304, 309, 311, 312, 313, 314, 317, 321, 324, 330, 333, 336, 341, 356, 360, 362, 365, 366, 370, 371, 372 and 373 may be identified by aligning the sequence of the variant polypeptide with that of SEQ ID NO: 4 using, for example, the GAP alignment to the most homologous sequence found by the GAP program (see below for details of this program). The positions in the variant corresponding to positions 35, 53, 63, 64, 65, 66, 74, 77, 79, 80, 81, 88, 106, 108, 111, 114, 117, 119, 122, 126, 161, 168, 181, 189, 190, 197, 205, 208, 211, 224, 228, 231, 232, 233, 236, 238, 250, 251, 254, 255, 259, 267, 270, 279, 282, 283, 286, 293, 297, 299, 300, 301, 303, 304, 309, 311, 312, 313, 314, 317, 321, 324, 330, 333, 336, 341, 356, 360, 362, 365, 366, 370, 371, 372 and 373 in SEQ ID NO: 4 may thus be identified and are referred to as those positions defined with reference to SEQ ID NO: 4.

In addition, a variant asparaginase polypeptide of the invention will typically not comprise one or more, for example, two, three or all of the amino acids corresponding to Asp 336, Thr 337, Ala 338 and Thr 339 in the wild-type asparaginase sequence obtained from *Aspergillus niger* as disclosed in WO 2004/030468. That is to say, when a variant asparaginase polypeptide of the invention is aligned with the wild-type asparaginase sequence obtained from *Aspergillus niger* as disclosed in WO 2004/030468, it will typically not comprise one or more of the amino acids corresponding to those found at positions 336, 337, 338 and 339 of the wild-type *A. niger* sequence.

In another embodiment the invention also provides an asparaginase having the width of the pH activity profile which is at least 3.5, preferably at least 4, more preferably at least 5 pH units wide. In a preferred embodiment the asparaginase having the width of the pH activity profile which is at least 3.5, preferably at least 4, more preferably at least 5 pH units wide, is an asparaginase according to a variant asparaginase having the amino acid sequence set out in any one of SEQ ID NO: 2 or SEQ ID NO: 4, and further variants thereof having at least 85% homology to at least one of them.

Polynucleotides

As set out above, the present invention provides polynucleotides encoding a variant asparaginase having an amino acid sequence according to any one of SEQ ID NO: 2 (tentatively called ASN001) or SEQ ID NO: 4 (tentatively called ASN002), and additional variants thereof, such as functional equivalents. Thus, the invention provides a polynucleotide according to any one of SEQ ID NO: 1 or SEQ ID NO: 3 and additional variant polynucleotides.

For the sake of clarity; SEQ ID NO: 1 is the polynucleotide sequence coding for the polypeptide according to SEQ ID NO: 2; SEQ ID NO: 3 is the polynucleotide sequence coding for the polypeptide according to SEQ ID NO: 4.

The invention provides polynucleotide sequences comprising the gene encoding asparaginases according to the invention as well as its coding sequence. Accordingly, the invention relates to a nucleic acid sequence which comprises:
a) a DNA sequence encoding the asparaginase according to any one of SEQ ID NO: 2 or SEQ ID NO: 4;
b) a DNA sequence encoding an asparaginase which has at least 85% homology with the polypeptide according to any one of SEQ ID NO: 2 or SEQ ID NO: 4;
c) a DNA sequence which has at least 80% homology with a DNA sequence according to a) or b);
d) a DNA sequence which hybridizes at high stringency with a complementary strand of a DNA sequence according to a) or b);
e) a subsequence of a DNA sequence according to a), b), c) or d) having at least 100 nucleotides; or
f) a complementary strand of a DNA sequence according to a), b), c), d) or e).

The invention also relates to an isolated polynucleotide encoding at least one functional domain of a polypeptide according to any one of SEQ ID NO: 2 or, SEQ ID NO: 4. Hereunder this is described more in detail for the polypeptides according to the invention.

Typically, regarding SEQ ID NO: 2, such a domain will comprise an amino acid or amino acids corresponding to one or more of Ala at position 25, Thr at position 28, Tyr at position 30, Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Ser at position 131, Val at position 161, Ala at position 168, Gln at position 181, Pro at position 189, Ala at position 190, Leu at position 197, Val at position 205, Phe at position 208, Ala at position 210, Ser at position 211, Val at position 224, Asn at position 228, Ala at position 231, Ile at position 232, Val at position 233, Lys at position 236, Tyr at position 238, Tyr at position 240, Thr at position 250, Thr at position 251, Val at position 252, Val at position 254, Arg at position 255, Ser at position 259, Tyr at position 267, Gln at position 270, Gln at position 273, Ser at position 279, Asp at position 282, Asn at position 283, Lys at position 286, Ser at position 293, Ser at position 297, Ser at position 299, Gly at position 301, Ser at position 303, Asp at position 304, Asp at 307, Ile at position 309, Ala at position 310, Ser at position 311, Lys at position 312, His at position 313, Ser at position 314, Ile at position 317, Leu at position 319, Thr at position 321, Gly at position 324, Thr at position 330, Phe at position 345, Ala at position 351, Ala at position 360, Glu at position 361, Gly at position 364, Phe at position 365, Lys at position 366, Arg at position 369, Glu at position 370, Lys at position 374, Val at position 375 or Val at position 377, said positions being defined with reference to SEQ ID NO: 2.

In one embodiment of the invention, the nucleic acid sequence according to the invention encodes a polypeptide, wherein the polypeptide is a variant comprising an amino acid sequence that has one or more truncation(s), and/or at least one substitution, deletion and/or insertion of an amino acid as compared to the sequence of amino acids 1 to 378 of SEQ ID NO: 2. Such a polypeptide will typically comprise one or more of Ala at position 25, Thr at position 28, Tyr at position 30, Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Ser at position 131, Val at position 161, Ala at position 168, Gln at position 181, Pro at position 189, Ala at position 190, Leu at position 197, Val at position 205, Phe at position 208, Ala at position 210, Ser at position 211, Val at position 224, Asn at position 228, Ala at position 231, Ile at position 232, Val at position 233, Lys at position 236, Tyr at position 238, Tyr at position 240, Thr at position 250, Thr at position 251, Val at position 252, Val at position 254, Arg at position 255, Ser at position 259, Tyr at position 267, Gln at position 270, Gln at position 273, Ser at position 279, Asp at position 282, Asn at position 283, Lys at position 286, Ser at position 293, Ser at position 297, Ser at position 299, Gly at position 301, Ser at position 303, Asp at position 304, Asp at 307, Ile at position 309, Ala at position 310, Ser at position 311, Lys at position 312, His at position 313, Ser at position 314, Ile at position 317, Leu at position 319, Thr at position 321, Gly at position 324, Thr at position 330, Phe at position 345, Ala at position 351, Ala at position 360, Glu at position 361, Gly at position 364, Phe at position 365, Lys at position 366, Arg at position 369, Glu at position 370, Lys at position 374, Val at position 375 or Val at position 377, said positions being defined with reference to SEQ ID NO: 2.

Typically, regarding SEQ ID NO: 4, such a domain will comprise an amino acid or amino acids corresponding to one or more of Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Val at position 161, Ala at position 168, Gln at position 181, Pro at position 189, Ala at position 190, Leu at position 197, Val at position 205, Phe at position 208, Ser at position 211, Val at position 224, Asn at position 228, Ala at position 231, Ile at position 232, Val at position 233, Lys at position 236, Tyr at position 238, Thr at position 250, Thr at position 251, Val at position 254, Arg at position 255, Ser at position 259, Tyr at position 267, Gln at position 270, Asp at position 279, Asp at position 282, Asn at position 283, Lys at position 286, Ser at position 293, Ser at position 297, Ser at position 299, Ser at position 300, Gly at position 301, Ser at position 303, Asp at position 304, Ile at position 309, Ser at position 311, Thr at position 312, His at position 313, Ser at position 314, Ile at position 317, Thr at position 321, Gly at position 324, Pro at position 330, Glu at position 333, Gln at position 336, Phe at position 341, Ala at position 356, Gly at position 360, Glu at position 362, Arg at position 365, Glu at position 366, Lys at position 370, Val at position 371, Gly at position 372 and Val at position 373, said positions being defined with reference to SEQ ID NO: 4.

In one embodiment of the invention, the nucleic acid sequence according to the invention encodes a polypeptide, wherein the polypeptide is a variant comprising an amino acid sequence that has one or more truncation(s), and/or at least one substitution, deletion and/or insertion of an amino acid as compared to the sequence of amino acids 1 to 374 of SEQ ID NO: 4. Such a polypeptide will typically comprise one or more of Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Val at position 161, Ala at position 168, Gln at position 181, Pro at position 189, Ala at position 190, Leu at position 197, Val at position 205, Phe at position 208, Ser at position 211, Val at position 224, Asn at position 228, Ala at position 231, Ile at position 232, Val at position 233, Lys at position 236, Tyr at position 238, Thr at position 250, Thr at position 251, Val at position 254, Arg at position 255, Ser at position 259, Tyr at position 267, Gln at position 270, Asp at position 279, Asp at position 282, Asn at position 283, Lys at position 286, Ser at position 293, Ser at position 297, Ser at position 299, Ser at position 300, Gly at position 301, Ser at position 303, Asp at position 304, He at position 309, Ser at position 311, Thr at position 312, His at position 313, Ser at position 314, He at position 317, Thr at position 321, Gly at position 324, Pro at position 330, Glu at position 333, Gln at position 336, Phe at position 341, Ala at position 356, Gly at position 360, Glu at position 362, Arg at position 365, Glu at position 366, Lys at position 370, Val at position 371, Gly at position 372 and Val at position 373, said positions being defined with reference to SEQ ID NO: 4.

In another embodiment the invention provides a nucleic acid molecule encoding an asparaginase having the width of the pH activity profile which is at least 3.5, preferably at least 4, more preferably at least 5 pH units wide. In a preferred embodiment said nucleic acid molecule encoding an asparaginase having the width of the pH activity profile which is at least 3.5 is a nucleic acid which comprises
> a) a DNA sequence encoding the asparaginase according to any one of SEQ ID NO: 2 or SEQ ID NO: 4;
> b) a DNA sequence encoding an asparaginase which has at least 85% homology with the polypeptide according to any one of SEQ ID NO: 2 or SEQ ID NO: 4;
> c) a DNA sequence which has at least 80% homology with a DNA sequence according to a) or b);
> d) a DNA sequence which hybridizes at high stringency with a complementary strand of a DNA sequence according to a) or b);
> e) a subsequence of a DNA sequence according to a), b), c) or d) having at least 100 nucleotides; or
> f) a complementary strand of a DNA sequence according to a), b), c), d) or e).

As used herein, the terms "gene" and "recombinant gene" refer to nucleic acid molecules which include an open reading frame encoding a variant asparaginase as described herein, e.g. a variant of wild-type *Aspergillus niger* asparaginase. A gene may include coding sequences, non-coding sequences, introns and regulatory sequences. That is to say, a "gene", as used herein, may refer to an isolated nucleic acid molecule as defined herein. Accordingly, the term "gene", in the context of the present application, does not refer only to naturally-occurring sequences.

A nucleic acid molecule of the present invention can be generated using standard molecular biology techniques well known to those skilled in the art taken in combination with the sequence information provided herein.

For example, using standard synthetic techniques, the required nucleic acid molecule may be synthesized de novo. Such a synthetic process will typically be an automated process. Such techniques are well-known to those skilled in the art.

Alternatively, a nucleic acid molecule of the invention may be generated by use of site-directed mutagenesis of an existing nucleic acid molecule, for example a wild-type nucleic acid molecule. Site directed mutagenesis may be carried out using a number of techniques well know to those skilled in the art.

In one such method, mentioned here merely by way of example, PCR is carried out on a plasmid template using oligonucleotide "primers" containing the desired mutation. As the primers are the ends of newly-synthesized strands, should there be a mis-match during the first cycle in binding the template DNA strand, after that first round, the primer-based strand (containing the mutation) would be at equal concentration to the original template. After successive cycles, it would exponentially grow, and after 25, would outnumber the original, unmutated strand in the region of 8 million: 1, resulting in a nearly homogeneous solution of mutated amplified fragments. The template DNA may then be eliminated by enzymatic digestion with, for example using a restriction enzyme which cleaves only methylated DNA, such as Dpn1. The template, which is derived from an alkaline lysis plasmid preparation and therefore is methylated, is destroyed in this step, but the mutated plasmid is preserved because it was generated in vitro and is unmethylated as a result.

In such a method more than one mutation may be introduced into a nucleic acid molecule in a single PCR reaction, for example by using one or more oligonucleotides, each comprising one or more mis-matches. Alternatively, more than one mutation may be introduced into a nucleic acid molecule by carrying out more than one PCR reaction, each reaction introducing one or more mutations, so that altered nucleic acids are introduced into the nucleic acid in a sequential, iterative fashion.

A nucleic acid of the invention can be generated using cDNA, mRNA or alternatively, genomic DNA, as a template and appropriate mis-matched oligonucleotide primers according to the site-directed mutagenesis technique described above. A nucleic acid molecule derived in this way can be cloned into an appropriate vector and characterized by DNA sequence analysis.

A nucleic acid sequence of the invention may comprise one or more deletions, i.e. gaps, in comparison to the wild-type sequence of the wild-type asparaginase sequence obtained from *Aspergillus niger* as disclosed in WO 2004/030468 and/or to the sequence set out in any one of SEQ ID NO: 2 or SEQ ID NO: 4. Such deletions/gaps may also be generated using site-directed mutagenesis using appropriate oligonucleotides. Techniques for generating such deletions are well known to those skilled in the art.

Furthermore, oligonucleotides corresponding to or hybridizable to nucleotide sequences according to the invention can be prepared by standard synthetic techniques, e.g., using an automated DNA synthesizer.

Also, complementary nucleic acid molecules are included in the present invention. A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a polypeptide of the invention or a functional equivalent thereof such as a biologically active fragment or domain, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules, such as for the preparation of nucleic acid molecules of the invention An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to a nucleic acid molecule of the invention, e.g., the coding strand of a nucleic acid molecule having the sequence set out in any one of SEQ ID NO: 1 or SEQ ID NO: 3. Also included within the scope of the invention are the complementary strands of the nucleic acid molecules described herein.

Identity & Homology

The terms "homology" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The nucleotide or the protein sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at http://www.ncbi.nlm.nih.gov/.

Hybridization

A polynucleotide of the invention and the complement of the sequence set out in any one of SEQ ID NO: 1 or SEQ ID NO: 3 can typically hybridize at a level significantly above background. Background hybridization may occur, for example, because of other cDNAs present in a cDNA library. The signal level generated by the interaction between a polynucleotide of the invention and the complement of the coding sequence of any one of SEQ ID NO: 1 or SEQ ID NO: 3 is typically at least 10 fold, preferably at least 100 fold, as intense as interactions between other polynucleotides and the sequence of any one of SEQ ID NO: 1 or SEQ ID NO: 3. The intensity of interaction may be measured, for example, by radiolabelling.

As used herein, the terms "hybridize" and "hybridizing" are intended to describe conditions for hybridization and washing under which nucleotide sequences at least about 60%, at least about 70%, preferably at least about 80%, more preferably at least about 85%, even more preferably at least about 90%, such as at least about 95% homologous to each other, for example at least about 98% homologous to each other, such as at least about 99% homologous to each other, as determined over a region of at least about 20, for instance at least about 50, such as at least about 100, for example at least about 200, more preferably at least about 300 contiguous nucleotides or more preferably over the full length of the sequences to be compared, typically remain hybridized to each other.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., preferably at 60° C. and even more preferably at 65° C.

Highly stringent conditions include, for example, hybridizing at 68° C. in 5×SSC/5×Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-standed cDNA clone).

Any combination of the above mentioned degrees of sequence identity and minimum sizes may be used to define polynucleotides of the invention, with more stringent combinations (i.e. higher sequence identify over longer lengths) being preferred.

Vectors

Another aspect of the invention pertains to vectors, preferably expression vectors, containing a nucleic acid encoding a variant asparaginase of the invention, for example the asparaginase protein of any one of SEQ ID NO: 2 or SEQ ID NO: 4 or a functional equivalent of any of them.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signal). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g. the asparaginase variant according to any one of SEQ ID NO: 2 or SEQ ID NO: 4 or a variant of any of them, for example a functional equivalent or fragment, or a fusion protein comprising one or more of such variants).

The recombinant expression vectors of the invention can be designed for expression of variant proteins of the invention in prokaryotic or eukaryotic cells. For example, a variant protein of the invention can be expressed in bacterial cells such as *E. coli*, insect cells (using baculovirus expression vectors) yeast cells or mammalian cells. Suitable host cells are discussed further in Goeddel, *Gene Expression Technology Methods in Enzymology* 185, Academic Press, San Diego, Calif. (1990).

Alternatively, the recombinant expression vector can be transcribed and translated in vitro, for example using T7 promoter regulatory sequences and T7 polymerase.

Expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled person. In a specific embodiment, promoters are preferred that are capable of directing a high expression level of asparaginase in filamentous fungi. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-percipitation, DEAE-dextran-mediated transfection, transduction, infection, lipofection, cationic lipidmediated transfection or electroporation. Suitable methods for transforming or transfecting host cells can be found in Sambrook, et al. (*Molecular Cloning: A Laboratory Manual, 2$^{nd}$, ed. Cold Spring Harbor Laboratory*, Cold Spring Harbor Laboratory Press, Cold Spring Harbor, N.Y., 1989), Davis et al., *Basic Methods in Molecular Biology* (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methatrexate. Nucleic acid encoding a selectable marker can be introduced into a host cell on the same vector as that encoding a variant protein of the invention or can be introduced on a separate vector. Cells stably transfected with the introduced nucleic acid can be identified by drug selection (e.g. cells that have incorporated the selectable marker gene will survive, while the other cells die).

Expression of proteins in prokaryotes is often carried out in *E. coli* with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

As indicated, the expression vectors will preferably contain selectable markers. Such markers include dihydrofolate reductase or neomycin resistance for eukaryotic cell culture and tetracyline or ampicillin resistance for culturing in *E. coli* and other bacteria. Representative examples of appropriate host include bacterial cells, such as *E. coli, Streptomyces Salmonella typhimurium* and certain *Bacillus* species; fungal cells such as *Aspergillus* species, for example *A. niger, A. oryzae* and *A. nidulans*, such as yeast such as *Kluyveromyces*, for example *K. lactis* and/or *Puchia*, for example *P. pastoris*; insect cells such as *Drosophila* S2 and *Spodoptera* Sf9; animal cells such as CHO, COS and Bowes melanoma; and plant cells. Appropriate culture mediums and conditions for the above-described host cells are known in the art.

Vectors preferred for use in bacteria are for example disclosed in WO-A1-2004/074468, which are hereby enclosed by reference. Other suitable vectors will be readily apparent to the skilled artisan.

Known bacterial promotors suitable for use in the present invention include the promoters disclosed in WI-A1-2004/074468, which are hereby incorporated by reference.

Transcription of the DNA encoding a variant of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretation signal may be incorporated into the expressed polypeptide. The signals may be endogenous to the polypeptide or they may be heterologous signals.

A variant of the invention may be expressed in form such that it may include additional heterologous functional regions, for example secretion signals. A variant of the invention may also comprise, for example, a region of additional amino acids, particularly charged amino acids, added to the N-terminus of the polypeptide for instance to improve stability and persistence in the host cell, during purification or during subsequent handling and storage. Also, peptide moieties may be added to a variant of the invention to facilitate purification, for example by the addition of histidine residues or a T7 tag.

Polypeptides According to the Invention

The invention provides an asparaginase which is:
 a) a polypeptide having an amino sequence, as shown in any one of SEQ ID NO: 2 or SEQ ID NO: 4;
 b) a polypeptide which has at least 85% homology with a polypeptide according to a);
 c) a polypeptide which can be obtained from a polypeptide defined in a) or b) by substitution, deletion, and/or insertion of one or more amino acids;
 d) a polypeptide which is encoded by a nucleic acid sequence of SEQ ID NO: 1 or SEQ ID NO: 3 encoding the mature polypeptide or a subsequence thereof having at least 100 nucleotides.

Typically, regarding SEQ ID NO: 2, a polypeptide according to b), c) or d) comprises one or more of Ala at position 25, Thr at position 28, Tyr at position 30, Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Ser at position 131, Val at position 161, Ala at position 168, Gln at position 181, Pro at position 189, Ala at position 190, Leu at position 197, Val at position 205, Phe at position 208, Ala at position 210, Ser at position 211, Val at position 224, Asn at position 228, Ala at position 231, Ile at position 232, Val at position 233, Lys at position 236, Tyr at position 238, Tyr at position 240, Thr at position 250, Thr at position 251, Val at position 252, Val at position 254, Arg at position 255, Ser at position 259, Tyr at position 267, Gln at position 270, Gln at position 273, Ser at position 279, Asp at position 282, Asn at position 283, Lys at position 286, Ser at position 293, Ser at position 297, Ser at position 299, Gly at position 301, Ser at position 303, Asp at position 304, Asp at 307, Ile at position 309, Ala at position 310, Ser at position 311, Lys at position 312, His at position 313, Ser at position 314, Ile at position 317, Leu at position 319, Thr at position 321, Gly at position 324, Thr at position 330, Phe at position 345, Ala at position 351, Ala at position 360, Glu at position 361, Gly at position 364, Phe at position 365, Lys at position 366, Arg at position 369, Glu at position 370, Lys at position 374, Val at position 375 or Val at position 377, said positions being defined with reference to SEQ ID NO: 2.

A polypeptide of the invention may comprise two or more of Ala at position 25, Thr at position 28, Tyr at position 30, Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Ser at position 131, Val at position 161, Ala at position 168, Gln at position 181, Pro at position 189, Ala at position 190, Leu at position 197, Val at position 205, Phe at position 208, Ala at position 210, Ser at position 211, Val at position 224, Asn at position 228, Ala at position 231, Ile at position 232, Val at position 233, Lys at position 236, Tyr at position 238, Tyr at position 240, Thr at position 250, Thr at position 251, Val at position 252, Val at position 254, Arg at position 255, Ser at position 259, Tyr at position 267, Gln at position 270, Gln at position 273, Ser at position 279, Asp at position 282, Asn at position 283, Lys at position 286, Ser at position 293, Ser at position 297, Ser at position 299, Gly at position 301, Ser at position 303, Asp at position 304, Asp at 307, Ile at position 309, Ala at position 310, Ser at position 311, Lys at position 312, His at position 313, Ser at position 314, Ile at position 317, Leu at position 319, Thr at position 321, Gly at position 324, Thr at position 330, Phe at position 345, Ala at position 351, Ala at position 360, Glu at position 361, Gly at position 364, Phe at position 365, Lys at position 366, Arg at position 369, Glu at position 370, Lys at position 374, Val at position 375 and Val at position 377, said positions being defined with reference to SEQ ID NO: 2. More preferably, a polypeptide of the invention may comprise all of those amino acids at the stated positions, said positions being defined with reference to SEQ ID NO: 2.

Regarding SEQ ID NO: 4, a polypeptide according to the invention may comprise one or more of Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Val at position 161, Ala at position 168, Gln at position 181, Pro at position 189, Ala at position 190, Leu at position 197, Val at position 205, Phe at position 208, Ser at position 211, Val at position 224, Asn at position 228, Ala at position 231, Ile at position 232, Val at position 233, Lys at position 236, Tyr at position 238, Thr at position 250, Thr at position 251, Val at position 254, Arg at position 255, Ser at position 259, Tyr at position 267, Gln at position 270, Asp at position 279, Asp at position 282, Asn at position 283, Lys at position 286, Ser at position 293, Ser at position 297, Ser at position 299, Ser at position 300, Gly at position 301, Ser at position 303, Asp at position 304, Ile at position 309, Ser at position 311, Thr at position 312, His at position 313, Ser at position 314, Ile at position 317, Thr at position 321, Gly at position 324, Pro at position 330, Glu at position 333, Gln at position 336, Phe at position 341, Ala at position 356, Gly at position 360, Glu at position 362, Arg at position 365, Glu at position 366, Lys at position 370, Val at position 371, Gly at position 372 or Val at position 373, said positions being defined with reference to SEQ ID NO: 4.

A polypeptide of the invention may comprise two or more of Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Val at position 161, Ala at position 168, Gln at position 181, Pro at position 189, Ala at position 190, Leu at position 197, Val at position 205, Phe at position 208, Ser at position 211, Val at position 224, Asn at position 228, Ala at position 231, Ile at position 232, Val at position 233, Lys at position 236, Tyr at position 238, Thr at position 250, Thr at position 251, Val at position 254, Arg at position 255, Ser at position 259, Tyr at position 267, Gln at position 270, Asp at position 279, Asp at position 282, Asn at position 283, Lys at position 286, Ser at position 293, Ser at position 297, Ser at position 299, Ser at position 300, Gly at position 301, Ser at position 303, Asp at position 304, Ile at position 309, Ser at position 311, Thr at position 312, His at position 313, Ser at position 314, Ile at position 317, Thr at position 321, Gly at position 324, Pro at position 330, Glu at position 333, Gln at position 336, Phe at position 341, Ala at position 356, Gly at position 360, Glu at position 362, Arg at position 365, Glu at position 366, Lys at position 370, Val at position 371, Gly at position 372 or Val at position 373, said positions being defined with reference to SEQ ID NO: 4.

More preferably, a polypeptide of the invention may comprise all of those amino acids at the stated positions, said positions being defined with reference to SEQ ID NO: 4.

In another embodiment the invention also provides an asparaginase having the width of the pH activity profile which is at least 3.5, preferably at least 4, more preferably at least 5 pH units wide. In a preferred embodiment the asparaginase having the width of the pH activity profile which is at least 3.5 is an asparaginase which is:
a) a polypeptide having an amino sequence, as shown in any one of SEQ ID NO: 2 or SEQ ID NO: 4;
b) a polypeptide which has at least 85% homology with a polypeptide according to a);
c) a polypeptide which can be obtained from a polypeptide defined in a) or b) by substitution, deletion, and/or insertion of one or more amino acids;
d) a polypeptide which is encoded by a nucleic acid sequence of SEQ ID NO: 1 or SEQ ID NO: 3 encoding the mature polypeptide or a subsequence thereof having at least 100 nucleotides.

Also, a peptide or polypeptide comprising a functional equivalent of the above polypeptides is comprised within the present invention. The above polypeptides are collectively comprised in the terms "a polypeptide according to the invention" or "a variant according to the invention".

The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (*Molecular Cloning: A Laboratory Manual, $2^{nd}$, ed. Cold Spring Harbor Laboratory*, Cold Spring Harbor Laboratory Press, Cold Spring Harbor, N.Y., 1989).

By "isolated" polypeptide or protein is intended a polypeptide or protein removed from its native environment. For example, recombinantly produced polypeptides and proteins expressed in host cells are considered isolated for the purpose of the invention as are native or recombinant polypeptides which have been substantially purified by any suitable technique such as, for example, the single-step purification method disclosed in Smith and Johnson, Gene 67:31-40 (1988).

A variant polypeptide according to the invention can be recovered and purified from recombinant cell cultures by methods known in the art. Most preferably, ion exchange chromatography or high performance liquid chromatography ("HPLC") is employed for purification.

Polypeptides of the present invention include products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Protein Fragments

The invention also features biologically active fragments of the polypeptides according to the invention. Such fragments are considered to be encompassed within the term "a variant of the invention".

Biologically active fragments of a polypeptide of the invention include polypeptides comprising amino acid sequences sufficiently identical to or derived from the amino acid sequence of a variant protein of the invention (e.g., the amino acid sequence of SEQ ID NO: 2 or SEQ ID NO: 4), which include fewer amino acids than the full length protein but which exhibit at least one biological activity of the corresponding full-length protein. Typically, biologically active fragments comprise a domain or motif with at least one activity of a variant protein of the invention. Preferably biologically active fragments will have at least asparaginase activity. A biologically active fragment of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

Typically, regarding SEQ ID NO: 2, a protein fragment of the invention will comprise one or more of Ala at position 25, Thr at position 28, Tyr at position 30, Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Ser at position 131, Val at position 161, Ala at position 168, Gln at position 181, Pro at position 189, Ala at position 190, Leu at position 197, Val at position 205, Phe at position 208, Ala at position 210, Ser at position 211, Val at position 224, Asn at position 228, Ala at position 231, Ile at position 232, Val at position 233, Lys at position 236, Tyr at position 238, Tyr at position 240, Thr at position 250, Thr at position 251, Val at position 252, Val at position 254, Arg at position 255, Ser at position 259, Tyr at position 267, Gln at position 270, Gln at position 273, Ser at position 279, Ser at position 282, Asn at position 283, Lys at position 286, Ser at position 293, Ser at position 297, Ser at position 299, Gly at position 301, Ser at position 303, Asp at position 304, Asp at 307, Ile at position 309, Ala at position 310, Ser at position 311, Lys at position 312, His at position 313, Ser at position 314, Ile at position 317, Leu at position 319, Thr at position 321, Gly at position 324, Thr at position 330, Phe at position 345, Ala at position 351, Ala at position 360, Glu at position 361, Gly at position 364, Phe at position 365, Lys at position 366, Arg at position 369, Glu at position 370, Lys at position 374, Val at position 375 and Val at position 377, said positions being defined with reference to SEQ ID NO: 2.

A protein fragment of the invention may comprise two or more of Ala at position 25, Thr at position 28, Tyr at position 30, Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Ser at position 131, Val at position 161, Ala at position 168, Gln at position 181, Pro at position 189, Ala at position 190, Leu at position 197, Val at position 205, Phe at position 208, Ala at position 210, Ser at position 211, Val at position 224, Asn at position 228, Ala at position 231, Ile at position 232, Val at position 233, Lys at position 236, Tyr at position 238, Tyr at position 240, Thr at position 250, Thr at position 251, Val at position 252, Val at position 254, Arg at position 255, Ser at position 259, Tyr at position 267, Gln at position 270, Gln at position 273, Ser at position 279, Asp at position 282, Asn at position 283, Lys at position 286, Ser at position 293, Ser at position 297, Ser at position 299, Gly at position 301, Ser at position 303, Asp at position 304, Asp at 307, Ile at position 309, Ala at position 310, Ser at position 311, Lys at position 312, His at position 313, Ser at position 314, Ile at position 317, Leu at position 319, Thr at position 321, Gly at position 324, Thr at position 330, Phe at position 345, Ala at position 351, Ala at position 360, Glu at position 361, Gly at position 364, Phe at position 365, Lys at position 366, Arg at position 369, Glu at position 370, Lys at position 374, Val at position 375 and Val at position 377, said positions being defined with reference to SEQ ID NO: 2. More preferably, a protein fragment of the invention may comprise all of those amino acids at the stated positions, said positions being defined with reference to SEQ ID NO: 2.

Typically, regarding SEQ ID NO: 4, a protein fragment of the invention will comprise one or more of Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Val at position 161, Ala at position 168, Gln at position 181, Pro at position 189, Ala at position 190, Leu at position 197, Val at position 205, Phe at position 208, Ser at position 211, Val at position 224, Asn at position 228, Ala at position 231, Ile at position 232, Val at position 233, Lys at position 236, Tyr at position 238, Thr at position 250, Thr at position 251, Val at position 254, Arg at position 255, Ser at position 259, Tyr at position 267, Gln at position 270, Asp at position 279, Asp at position 282, Asn at position 283, Lys at position 286, Ser at position 293, Ser at position 297, Ser at position 299, Ser at position 300, Gly at position 301, Ser at position 303, Asp at position 304, Ile at position 309, Ser at position 311, Thr at position 312, His at position 313, Ser at position 314, Ile at position 317, Thr at position 321, Gly at position 324, Pro at position 330, Glu at position 333, Gln at position 336, Phe at position 341, Ala at position 356, Gly at position 360, Glu at position 362, Arg at position 365, Glu at position 366, Lys at position 370, Val at position 371, Gly at position 372 and Val at position 373, said positions being defined with reference to SEQ ID NO: 4.

A protein fragment of the invention may comprise two or more of Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Val at position 161, Ala at position 168, Gln at position 181, Pro at position 189, Ala at position 190, Leu at position 197, Val at position 205, Phe at position 208, Ser at position 211, Val at position 224, Asn at position 228, Ala at position 231, Ile at position 232, Val at position 233, Lys at position 236, Tyr at position 238, Thr at position 250, Thr at position 251, Val at position 254, Arg at position 255, Ser at position 259, Tyr at position 267, Gln at position 270, Asp at position 279, Asp at position 282, Asn at position 283, Lys at position 286, Ser at position 293, Ser at position 297, Ser at position 299, Ser at position 300, Gly at position 301, Ser at position 303, Asp at position 304, Ile at position 309, Ser at position 311, Thr at position 312, His at position 313, Ser at position 314, Ile at position 317, Thr at position 321, Gly at position 324, Pro at position 330, Glu at position 333, Gln at position 336, Phe at position 341, Ala at position 356, Gly at position 360, Glu at position 362, Arg at position 365, Glu at position 366, Lys at position 370, Val at position 371, Gly at position 372 and Val at position 373, said positions being defined with reference to SEQ ID NO: 4. More preferably, a protein fragment of the invention may comprise all of those amino acids at the stated positions, said positions being defined with reference to SEQ ID NO: 4.

The invention also features nucleic acid fragments which encode the above biologically active fragments (which biologically active fragments are themselves variants of the invention).

Fusion Proteins

The variants of the invention, such as proteins of the present invention or functional equivalents thereof, e.g., biologically active portions and fragments thereof, can be operatively linked to a polypeptide not according to the invention (e.g., heterologous amino acid sequences) to form fusion proteins. A polypeptide not according to the invention in this context refers to a polypeptide having an amino acid sequence corresponding to a protein which is not substantially homologous to a variant asparaginase of the invention.

Within a fusion protein, the variant of the invention can correspond to a full length sequence or a biologically active fragment of a polypeptide of the invention. In a preferred embodiment, a fusion protein of the invention comprises at least two biologically active portions. Within the fusion protein, the term "operatively linked" is intended to indicate that the variant polypeptide and the polypeptide not according to the invention are fused in-frame to each other. The polypeptide not according to the invention can be fused to the N-terminus or C-terminus of the variant polypeptide.

For example, in one embodiment, the fusion protein is a fusion protein in which the variant sequence/s is/are fused to the C-terminus of the GST sequences. Such fusion proteins can facilitate the purification of a recombinant variant according to the invention. In another embodiment, the fusion protein is a variant of the invention containing a heterologous signal sequence at its N-terminus. In certain host cells (e.g., mammalian and yeast host cells), expression and/or secretion of a variant of the invention can be increased through use of a heterologous signal sequence.

In another example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokarytic heterologous signal sequences include the phoA secretory signal (Sambrook et al., supra) and the protein A secretory signal (Pharmacia Biotech; Piscataway, N.J.).

A signal sequence can be used to facilitate secretion and isolation of a variant of the invention. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. The signal sequence may direct secretion of the variant, such as from a eukaryotic host into which the expression vector is transformed, and the signal sequence may then be subsequently or concurrently cleaved. The variant of the invention may then be readily purified from the extracellular medium by known methods. Alternatively, the signal sequence can be linked to the variant of interest using a sequence, which facilitates purification, such as with a GST domain. Thus, for instance, the sequence encoding the variant of the invention may be fused to a marker sequence, such as a sequence encoding a peptide, which facilitates purification of the fused variant of the invention. In certain preferred embodiments of this aspect of the invention, the marker sequence is a hexa-histidine peptide, such as the tag provided in a pQE vector (Qiagen, Inc.), among others, many of which are commercially available. As described in Gentz et al, *Proc. Natl. Acad. Sci. USA* 86:821-824 (1989), for instance, hexahistidine provides for convenient purification of the fusion protein. The HA tag is another peptide useful for purification which corresponds to an epitope derived of influenza hemaglutinin protein, which has been described by Wilson et al., *Cell* 37:767 (1984), for instance.

A fusion protein of the invention may be produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers, which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g, a GST polypeptide). A variant-encoding nucleic acid can be cloned into such an expression vector such that the fusion moiety is linked in-frame to the said variant.

Functional Equivalents

The terms "functional equivalents" and "functional variants" are used interchangeably herein. Functional equivalents according to the invention are isolated DNA fragments that encode a polypeptide that exhibits a particular function of the *Aspergillus niger* asparaginase variants as defined herein. A functional equivalent of a polypeptide according to the invention is a polypeptide that exhibits at least one function of an *Aspergillus niger* asparaginase variant as defined herein. Functional equivalents therefore also encompass biologically active fragments and are themselves encompassed within the term "a variant" of the invention.

Preferably, a functional equivalent polypeptide regarding SEQ ID NO: 2 of the invention comprises one or more of Ala at position 25, Thr at position 28, Tyr at position 30, Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Ser at position 131, Val at position 161, Ala at position 168, Gln at position 181, Pro at position 189, Ala at position 190, Leu at position 197, Val at position 205, Phe at position 208, Ala at position 210, Ser at position 211, Val at position 224, Asn at position 228, Ala at position 231, Ile at position 232, Val at position 233, Lys at position 236, Tyr at position 238, Tyr at position 240, Thr at position 250, Thr at position 251, Val at position 252, Val at position 254, Arg at position 255, Ser at position 259, Tyr at position 267, Gln at position 270, Gln at position 273, Ser at position 279, Asp at position 282, Asn at position 283, Lys at position 286, Ser at position 293, Ser at position 297, Ser at position 299, Gly at position 301, Ser at position 303, Asp at position 304, Asp at 307, Ile at position 309, Ala at position 310, Ser at position 311, Lys at position 312, His at position 313, Ser at position 314, Ile at position 317, Leu at position 319, Thr at position 321, Gly at position 324, Thr at position 330, Phe at position 345, Ala at position 351, Ala at position 360, Glu at position 361, Gly at position 364, Phe at position 365, Lys at position 366, Arg at position 369, Glu at position 370, Lys at position 374, Val at position 375 or Val at position 377, said positions being defined with reference to SEQ ID NO: 2.

Accordingly, a variant asparaginase polypeptide of the invention may comprise two, three, four, five, for example at least 10, at least 15, at least 20, such as at least 25, at least 30, at least 40, at least 50, at least 60, at least 70, at least 80 or all of Ala at position 25, Thr at position 28, Tyr at position 30, Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Ser at position 131, Val at position 161, Ala at position 168, Gln at position 181, Pro at position 189, Ala at position 190, Leu at position 197, Val at position 205, Phe at position 208, Ala at position 210, Ser at position 211, Val at position 224, Asn at position 228, Ala at position 231, Ile at position 232, Val at position 233, Lys at position 236, Tyr at position 238, Tyr at position 240, Thr at position 250, Thr at position 251, Val at position 252, Val at position 254, Arg at position 255, Ser at position 259, Tyr at position 267, Gln at position 270, Gln at position 273, Ser at position 279, Asp at position 282, Asn at position 283, Lys at position 286, Ser at position 293, Ser at position 297, Ser at position 299, Gly at position 301, Ser at position 303, Asp at position 304, Asp at 307, Ile at position 309, Ala at position 310, Ser at position 311, Lys at position 312, His at position 313, Ser at position 314, Ile at position 317, Leu at position 319, Thr at position 321, Gly at position 324, Thr at position 330, Phe at position 345, Ala at position 351, Ala at position 360, Glu at position 361, Gly at position 364, Phe at position 365, Lys at position 366, Arg at position 369, Glu at position 370, Lys at position 374, Val at position 375 or Val at position 377, said positions being defined with reference to SEQ ID NO: 2.

Preferably, a functional equivalent polypeptide regarding SEQ ID NO: 4 of the invention comprises one or more of Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Val at position 161, Ala at position 168, Gln at position 181, Pro at position 189, Ala at position 190, Leu at position 197, Val at position 205, Phe at position 208, Ser at position 211, Val at position 224, Asn at position 228, Ala at position 231, He at position 232, Val at position 233, Lys at position 236, Tyr at position 238, Thr at position 250, Thr at position 251, Val at position 254, Arg at position 255, Ser at position 259, Tyr at position 267, Gln at position 270, Asp at position 279, Asp at position 282, Asn at position 283, Lys at position 286, Ser at position 293, Ser at position 297, Ser at position 299, Ser at position 300, Gly at position 301, Ser at position 303, Asp at position 304, Ile at position 309, Ser at position 311, Thr at position 312, His at position 313, Ser at position 314, Ile at position 317, Thr at position 321, Gly at position 324, Pro at position 330, Glu at position 333, Gln at position 336, Phe at position 341, Ala at position 356, Gly at position 360, Glu at position 362, Arg at position 365, Glu at position 366, Lys at position 370, Val at position 371, Gly at position 372 and Val at position 373, said positions being defined with reference to SEQ ID NO: 4.

Accordingly, a variant asparaginase polypeptide of the invention may comprise two, three, four, five, for example at least 10, at least 15, at least 20, such as at least 25, at least 30, at least 40, at least 50, at least 60, at least 70 or all of Ser at position 35, Leu at position 53, Ser at position 63, Ala at position 64, Asp at position 65, Asn at position 66, Ala at position 74, Ile at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Val at position 161, Ala at position 168, Gln at position 181, Pro at position 189, Ala at position 190, Leu at position 197, Val at position 205, Phe at position 208, Ser at position 211, Val at position 224, Asn at position 228, Ala at position 231, Ile at position 232, Val at position 233, Lys at position 236, Tyr at position 238, Thr at position 250, Thr at position 251, Val at position 254, Arg at position 255, Ser at position 259, Tyr at position 267, Gln at position 270, Asp at position 279, Asp at position 282, Asn at position 283, Lys at position 286, Ser at position 293, Ser at position 297, Ser at position 299, Ser at position 300, Gly at position 301, Ser at position 303, Asp at position 304, Ile at position 309, Ser at position 311, Thr at position 312, His at position 313, Ser at position 314, Ile at position 317, Thr at position 321, Gly at position 324, Pro at position 330, Glu at position 333, Gln at position 336, Phe at position 341, Ala at position 356, Gly at position 360, Glu at position 362, Arg at position 365, Glu at position 366, Lys at position 370, Val at position 371, Gly at position 372 and Val at position 373, said positions being defined with reference to SEQ ID NO: 4.

Functional protein or polypeptide equivalents may contain substitutions of one or more amino acids of any one of SEQ ID NO: 2 or SEQ ID NO: 4 or substitutions, insertions or deletions of non-essential amino acids. Accordingly, a non-essential amino acid is a residue that can be altered in any one of SEQ ID NO: 2 or SEQ ID NO: 4 without substantially altering the biological function. Furthermore, amino acids conserved among the proteins according to the present invention and other asparaginases are not likely to be amenable to alteration.

Amino acid substitutions may be made to any one of SEQ ID NO: 2 or, SEQ ID NO: 4 for example from 1, 2 or 3 to about 10, about 20, about 30 or more substitutions, to provide a functional variant of the invention.

Functional nucleic acid equivalents may typically contain silent mutations or mutations that do not alter the biological function of encoded polypeptide. Accordingly, the invention provides nucleic acid molecules encoding a variant asparaginase protein that contains changes in amino acid residues that are not essential for a particular biological activity. Such variant proteins differ in amino acid sequence from any one of SEQ ID NO: 2 or SEQ ID NO: 4, yet retain at least one biological activity thereof. In one embodiment the isolated nucleic acid molecule comprises a nucleotide sequence encoding a protein, wherein the protein comprises a substantially homologous amino acid sequence of at least about 85%, 90%, 95%, 96%, 97%, 98%, 99% or more homologous to the amino acid sequence shown in any one of SEQ ID NO: 2 or SEQ ID NO: 4, An isolated nucleic acid molecule encoding a variant of the invention which is homologous, typically substantially homologous, to the protein according to any one of SEQ ID NO: 2 or SEQ ID NO: 4 can be created by introducing one or more nucleotide substitutions, additions or deletions into the coding nucleotide sequences according to the invention such that one or more amino acid substitutions, deletions or insertions are introduced into the encoded protein. Such mutations may be introduced by standard techniques, such as site-directed mutagenesis and PCR-mediated mutagenesis.

As defined herein, the term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain having about 60%, preferably 65%, more preferably 70%, even more preferably 75%, 80%, 85%, 90%, 95%, 96%, 97%, 98% or 99% identity or more are defined herein as sufficiently identical.

Nucleic acid molecules corresponding to, i.e. encoding, variant asparaginases of the invention can be isolated based on their homology to the nucleic acids of the invention disclosed herein using the cDNAs disclosed herein.

The skilled person will recognise that changes can be introduced by mutation into the nucleotide sequences according to the invention thereby leading to changes in the amino acid sequence of the resulting protein without substantially altering the function of such a protein.

In another aspect of the invention, improved asparaginase variant proteins are provided. Improved asparaginase variant proteins are proteins wherein at least one biological activity is improved, for example in comparison to a wild-type asparaginase, such as that from *A. niger*.

In particular, variant proteins of the invention may have improved specific activity at a given pH in comparison to a wild-type asparaginase such as that from *A. niger* as disclosed in SEQ ID NO: 3 of WO 2004/030468 or may have an improved pH response, for example be more alkaliphilic or acidophilic, in comparison to a wild-type asparaginase such as that from *A. niger* as disclosed in SEQ ID NO: 3 of WO 2004/030468. For example variant proteins of the invention may have a specific activity at pH at least 5 which is higher in comparison to the specific activity of the wild-type asparaginase from *A. niger* as disclosed in SEQ ID NO: 3 of WO 2004/030468 measured under the same conditions. For example, the wild-type asparaginase from *A. niger* as disclosed in SEQ ID NO: 3 of WO 2004/030468 has a pH optimum of from pH 4 to pH 5. A variant protein of the invention may be more alkaliphilic than such a wild-type enzyme, i.e. may, for example, have a pH optimum of from pH 6 to pH 7. A variant may though be more acidophilic than a wild-type asparaginase.

In another embodiment variant proteins of the invention may have the width of the pH activity profile which is at least 3.5, preferably at least 4, more preferably at least 5 pH units wide.

Such proteins may be obtained by randomly introducing mutations along all or part of a coding sequence of the invention, such as by saturation mutagenesis. The resulting mutants can then be expressed recombinantly and screened for biological activity. For instance, the art provides for standard assays for measuring the enzymatic activity of asparaginase and thus improved proteins may easily be selected.

In a preferred embodiment the asparaginase variant of the invention has an amino acid sequence according to any one of SEQ ID NO: 2 or SEQ ID NO: 4. In another embodiment, a variant of the invention is substantially homologous to the amino acid sequence according to any one of SEQ ID NO: 2 or SEQ ID NO: 4 and typically also retains at least one biological activity of the polypeptide according to any one of SEQ ID NO: 2 or SEQ ID NO: 4, yet may differs in amino acid sequence due to mutagenesis as described above.

In a further preferred embodiment, an asparaginase variant of the invention has an amino acid sequence encoded by an isolated nucleic acid fragment capable of hybridizing to a nucleic acid according to the invention, preferably under highly stringent hybridization conditions.

Accordingly, an asparaginase variant of the invention is preferably a protein which comprises an amino acid sequence at least about 85%, 90%, 95%, 96%, 97%, 98%, 99% or more homologous to the amino acid sequence shown in any one of SEQ ID NO: 2 or SEQ ID NO: 4 and retains at least one functional activity of the polypeptide according to any one of SEQ ID NO: 2 or SEQ ID NO: 4.

Variants of the invention, for example functional equivalents of a protein according to the invention, can also be identified e.g. by screening combinatorial libraries of mutants, e.g. truncation mutants, of the protein of the invention for asparaginase activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g. for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the sequence encoding a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3): 327-331).

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides can be used as hybridization probes or polymerase chain reaction (PCR) primers. Uses of the nucleic acid molecules of the present invention that do not encode a polypeptide having asparaginase activity include, inter alia, (1) in situ hybridization (e.g. FISH) to metaphase chromosomal spreads to provide precise chromosomal location of an asparaginase-encoding gene as described in Verma et al., Human Chromosomes: a Manual of Basic Techniques, Pergamon Press, New York (1988); (2) Northern blot analysis for detecting expression of asparaginase mRNA in specific tissues and/or cells; and (3) probes and primers that can be used as a diagnostic tool to analyse the presence of a nucleic acid hybridizable to such a probe or primer in a given biological (e.g. tissue) sample.

Also encompassed by the invention is a method of obtaining a functional equivalent of a polynucleotide of the invention. Such a method entails obtaining a labelled probe that includes an isolated nucleic acid which encodes all or a portion of the protein sequence according to any one of SEQ ID NO: 2 or SEQ ID NO: 4 or a variant thereof, screening a nucleic acid fragment library with the labelled probe under conditions that allow hybridization of the probe to nucleic acid fragments in the library, thereby forming nucleic acid duplexes, and preparing a full-length gene sequence from the nucleic acid fragments in any labelled duplex to obtain a sequence related to a polynucleotide of the invention.

Host Cells

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are cells from filamentous fungi, in particular *Aspergillus niger*.

A host cell can be chosen that modulates the expression of the inserted sequences, or modifies and processes the product encoded by the incorporated nucleic acid sequence in a specific, desired fashion. Such modifications (e.g., glycosylation) and processing (e.g., cleavage) of protein products may facilitate optimal functioning of the encoded protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

Host cells also include, but are not limited to, mammalian cell lines such as CHO, VERO, BHK, HeLa, COS, MDCK, 293, 3T3, WI38, and choroid plexus cell lines.

If desired, a stably transfected cell line can produce a variant according to the invention. A number of vectors suitable for stable transfection of mammalian cells are available to the public, methods for constructing such cell lines are also publicly known, e.g., in Ausubel et al. (supra).

Use of a Variant Asparaginase of the Invention in Industrial Processes

The present invention further discloses a composition comprising the asparaginases according to the invention. The composition may optionally comprise other ingredients, e.g. other enzymes. The asparaginase variants according to the invention or compositions comprising said asparaginases can be used in the production of a food product. In one embodiment of the invention the asparaginase variants according to the invention or compositions comprising said asparaginases can be used to reduce the amount of acrylamide formed in a thermally process food product based on an asparagine containing raw material. They can for example, be used in a process for the production of a food product involving at least one heating step, comprising adding one or more asparaginase enzymes to an intermediate form of said food product in said production process whereby the enzyme is added prior to said heating step in an amount that is effective in reducing the level of asparaginase that is present in said intermediate form of said food product. Such process is disclosed in WO04/030468 which process and all its preferences are herein incorporated by reference. Also in WO04/026043 suitable processes are described wherein the asparaginase according to the invention could be used. The processes disclosed in WO04/026043 and all preferences disclosed are herein incorporated by reference.

An intermediate form of the food product is defined herein as any form that occurs during the production process prior to obtaining the final form of the food product. The intermediate form may comprise the individual raw materials used and/or mixture thereof and/or mixtures with additives and/or processing aids, or subsequently processed form thereof. For example, for the food product bread, the intermediate forms comprise for example wheat, wheat flour, the initial mixture thereof with other bread ingredients such as for example water, salt, yeast and bread improving compositions, the mixed dough, the kneaded dough, the leavened dough and the partially baked dough. For example for several potato-based products, dehydrated potato flakes or granules are intermediate products, and corn masa is an intermediate product for tortilla chips.

The food product may be made from at least one raw material that is of plant origin, for example potato, tobacco, coffee, cocoa, rice, cereal, for example wheat, rye corn, maize, barley, groats, buckwheat and oat. Wheat is here and hereafter intended to encompass all known species of the *Triticum* genus, for example aestivum, durum and/or spelta. Also food products made from more than one raw material or intermediate are included in the scope of this invention, for example food products comprising both wheat (flour and/or starch) and potato. Examples of food products in which the process according the invention can be suitable for are any flour based products—for example bread, pastry, cake, pretzels, bagels, Dutch honey cake, cookies, gingerbread, gingercake and crispbread—, and any potato-based products—for example French fries, pommes frites, potato chips, croquettes.

Raw materials as cited above are known to contain substantial amounts of asparagine which is involved in the formation of acrylamide during the heating step of the production process. Alternatively, the asparagine may originate from other sources than the raw materials e.g. from protein hydrolysates, such as yeast extracts, soy hydrolysate, casein hydrolysate and the like, which are used as an additive in the food production process. A preferred production process is the baking of bread and other baked products from wheat flour and/or flours from other cereal origin. Another preferred production process is the deep-frying of potato chips from potato slices.

Preferred heating steps are those at which at least a part of the intermediate food product, e.g. the surface of the food product, is exposed to temperatures at which the formation of acrylamide is promoted, e.g. 110° C. or higher, 120° C. or higher temperatures. The heating step in the process according to the invention may be carried out in ovens, for instance at a temperature between 180-220° C., such as for the baking of bread and other bakery products, or in oil such as the frying of potato chips, for example at 160-190° C.

In another aspect, the invention provides food products obtainable by the process of the invention as described hereinbefore or by the use of the novel asparaginase as described hereinbefore to produce food products. These food products are characterized by significantly reduced acrylamide levels in comparison with the food products obtainable by production processes that do not comprise adding one or more enzymes in an amount that is effective in reducing the level of amino acids which are involved in the formation of acrylamide during said heating step. The process according to the invention can be used to obtain a decrease of the acrylamide content of the produced food product preferably more than 50%, more preferably more than 20%, even more preferably 10% and most preferably more than 5% compared to a food product obtained with the conventional process.

An additional application for the asparaginase variants according to the invention is to be employed in the therapy of tumours in animals and humans. The metabolism of tumour cells requires L-asparagine, which can quickly be degraded by asparaginases. The asparaginase according to the invention can also be used as an adjunct in treatment of some human leukaemia. Administration of asparaginase in experimental animals and humans leads to regression of certain lymphomas and leukemia. Therefore in one embodiment the invention relates to asparaginases or a composition according to the invention for use as medicament, e.g. in the treatment of tumors, e.g. in the treatment of lymphomas or leukaemia in animals or humans.

Asparaginase variants according to the invention may conveniently be produced in microorganisms. In the above processes, it is advantageous to use asparaginases that are obtained by recombinant DNA techniques. Such recombinant enzymes have a number of advantages, such as production at a low cost price, high yield, free from contaminating agents such as bacteria or viruses, but also free from bacterial toxins or contaminating other enzyme activities.

The invention is hereinafter illustrated by the following non-limiting Examples.

EXAMPLES

Materials & Methods
Asparaginase Assay in Order to Measure pH Dependence in Range pH=4 to pH=9

The asparaginase activity was measured using L-asparagine as substrate. The amount of ammonia that was liberated by the action of the enzyme was measured according to the Berthelot reaction. Ready-to-use reagents phenolnitroprusside and alkaline hypoclorite were obtained from Sigma. 100 µl enzyme sample was mixed with 2000 µl 100 mM L-asparagine in a mixture of 50 mM citric acid and 50 mM sodium pyrophosphate buffer of the desired pH. After incubation at 37° C. for 30 minutes the reaction was stopped by adding 400 µl 25% trichloroacetic acid, whereafter 2500 µl water was added. During the incubation the temperature was fixed at 37° C. unless indicated otherwise.

It should be understood by a person skilled in the art that enzyme dosing was chosen in such a way that after incubation under the above conditions a signal was obtained significantly above the background but still within a range where the signals obtained are proportional to the amount of enzyme added. Preferably the reaction was zero order.

After stopping the reaction, 4 µl of the incubation mixture was added to 156 µl water. Subsequently 34 µl phenol/nitroprusside solution (Sigma P6994) and 34 µl alkaline hypochlorite solution (Sigma A1727) were added. After 676 seconds of incubation at 37° C., the extinction was measured at 600 nm. Readings were corrected for the background signal by including the appropriate blanks. A sample with (TCA) inactivated enzyme was used as a blank. The assays were run on an autoanalyzer e.g. a Konelab Arena 30 (Thermo Scientific). The activity was determined using a calibration line made up by plotting the measured absorbance at 600 nm versus the known ammonium sulphate concentrations of a standard series. Activity was expressed in units, where one unit is defined as the amount of enzyme required to liberate one micromole of ammonia from L-asparagine per minute under defined assay conditions.

Asparaginase Assay in Order to Measure pH Dependence in Range pH=4 to pH=8

The method was executed in the same way as to the method described above for measurement of pH dependence of the activity for the range pH=4 to pH=9, with the difference that 100 µl enzyme sample was mixed with 2000 µl 100 mM L-asparagine in a 50 mM phosphate/citric acid buffer of the desired pH.

In all assays the activity of the asparaginase samples were expressed in unit/ml.

Example 1

Fermentation, Isolation and Purification of Asparaginases According to the Invention Asparaginases of the invention were obtained by the construction of expression plasmids containing a DNA sequence encoding the asparaginase of the invention, transforming an *Aspergillus niger* strain with the plasmid and growing the *Aspergillus niger* strains as described in WO2004/030468.

After growing *Aspergillus niger* containing the proper expression plasmids cell free supernatants were prepared by centrifugation of the fermentation broth at 5000×g for 30 minutes at 4° C. If necessary the supernatants were filtered further over a Miracloth filter (Calbiochem cat#475855) and a GF/A Whatmann Glass microfiber filter (150 mm Ø), respectively, to remove any solids. To remove any fungal material the supernatants could be adjusted to pH=5 with 4N KOH and sterile filtrated over a 2 µm (bottle-top) filter with suction. The supernatants were stored until use at 4° C. or frozen at −20° C. if necessary.

In case impurities were more than 60% w/w asparaginase were purified by anion ion-exchange chromatography starting from cell free supernatants or ccUF desalted via a PD-10 column (Amersham Biosciences). The desalted material was applied to a Mono-Q or Q-Sepharose column equilibrated in 20 mM histidine buffer pH 5.96. After extensive washing the asparaginases were eluted from the column using a gradient from 0 to 1M NaCl.

The purity of the supernatant fractions containing the asparaginase activity or of the purified asparaginase fractions (determined in mg protein/ml) was checked by analytical size-exclusion chromatography (HP-SEC: High Performance Size Exclusion Chromatography, TSKgel 3000SW-XL, column 300*7.8 mm; MW range 10-300 kDa, 100 mM phosphate buffer pH7 and pH5.96). All flows were 1 ml/min (except for sample injection on the Q-Sepharose column, which was at 5 ml/min). Detection of eluted proteins was done at 280 nm. The concentration of the eluted *Aspergillus niger* asparaginases was calculated from the extinction at 280 nm (A280) using a molar extinction coefficient of 10240 $M^{-1}.cm^{-1}$ ($A280^{1cm,1mg/ml}$=0.28, wherein $A280^{1cm/ml}$ is the extinction at 280 nm measured with a path length of 1 cm and at a concentration of pure protein of 1 mg/ml). Measurement of the A280 was performed in a Uvikon XL Secomam spectrophotometer (Beun de Ronde, Abcoude, The Netherlands). For asparaginase corresponding to SEQ ID NO: 4 (ASN002) and asparaginase corresponding to SEQ ID NO: 2 (ASN001) respectively 8960 $M^{-1}.cm^{-1}$ (A2801 $cm^{1cm,1mg/ml}$=0.25) and 11520 $M^{-1}.cm^{-1}$ ($A280^{1cm/1mg/ml}$=0.31) were used. In case of impurities absorbing at 280 nm the asparaginase concentration was corrected based on the HP-SEC chromatogram by multiplying the measured A280 of the asparaginase sample by the ratio of the area under the asparaginase peak and the total area of the peaks absorbing at 280 nm. When the asparaginase peaks was not clearly separated from other peaks the peak heights instead of peak areas were taken.

Example 2

Performance of Asparaginase According to the Invention

Specific Activity as a Function of pH

The specific activity of the asparaginase variants was determined at pH=4, pH=5, pH=6, pH=7, pH=8 at 37° C. in 50 mM phosphate/citrate buffer using cell-free supernatants. Specific enzyme activity, is herewith defined as the activity determined for an enzyme sample in units/mg of pure enzyme polypeptide. Specific asparaginase activity is therefore the activity determined for an asparaginase sample in units/mg of pure asparaginase polypeptide.

TABLE 1

The specific activity of the variants relative to wild type (wt) *A. niger* asparaginase (WO2004/030468) using asparagine as a substrate at the indicated pH values. For each pH the wild type specific activity is set to 100%. Activity was determined at 37° C.

|  | pH = 4 (%) | pH = 5 (%) | pH = 6 (%) | pH = 7 (%) | pH = 8 (%) |
|---|---|---|---|---|---|
| wt | 100 | 100 | 100 | 100 | 100 |
| ASN002 | 14 | 125 | 226 | 374 | 1033 |
| ASN001 | 55 | 246 | 418 | 697 | 1758 |

For determination of the specific activity the asparaginase, concentration in the supernatant was derived from an A280 measurement applying a correction for any impurities based on HP-SEC chromatography as indicated in material and methods.

Relative to wild type the pH optimum of variants ASN002 and ASN001 has shifted from pH=4 to pH=6. In addition the pH optimum has become much broader, in particular in the alkaline range. The variants ASN002 and ASN001 show for all the measured pH values beyond pH=4 a substantially higher specific activity compared to wild type.

The pH-Activity Dependence and the pH Optimum

The pH dependence of the asparaginase activity was determined in 50 mM phosphate/citrate buffer for the pH range pH=4 to pH=8 using cell-free supernatants. The pH at which the highest activity was observed for a variant is called the pH optimum for the said variant. In table 2 the maximum activity observed for a variant is set to 100% and activities of said variant at other pH values are shown as percentage of the maximum activity observed for said variant.

TABLE 2

The pH dependence of the asparaginase activity for the variants compared to wild type (wt) *A. niger* asparaginase (WO2004/030468). The highest activity that was observed for each asparaginase was set to 100%. Activity was determined at 37° C.

|  | pH = 4 (%) | pH = 5 (%) | pH = 6 (%) | pH = 7 (%) | pH = 8 (%) |
|---|---|---|---|---|---|
| wt | 100 | 98 | 71 | 42 | 15 |
| ASN002 | 9 | 76 | 100 | 95 | 90 |
| ASN001 | 19 | 81 | 100 | 95 | 83 |

Table 2 shows that the pH optimum has shifted to a higher pH. In addition the activity at alkaline pH is significantly improved for the variants, which makes these variants very useful for applications that require aspargainase activity under more alkaline conditions.

Width of the pH Activity Profile of the Variants

The most remarkable feature of ASN002 and ASN001 is that the two asparaginases exhibit an extremely broad pH-activity profile in the most useful pH range pH=4 to pH=9, which has not been observed for any aparaginase before. In order to establish the width of the pH-activity profile the activity was determined over for pH=4 to pH=9, using a citric acid/pyrophosphate buffer. The width of the pH-activity profile is the width of the pH range, calculated in pH units, where the enzyme exhibits 50% to 100% of its maximal activity. The width of the pH-activity profile is determined by plotting the activity against the pH. The width of the pH range calculated in pH units, for which the enzyme exhibits at least 50% of its maximal activity defines the width of the pH-activity profile of said enzyme. When a line is drawn parallel to the pH axis at half of the maximal activity, the pH-activity profile intersects at two pH values with this line. The two intersection pH values, one for the acidic limb and one for the alkaline limb of the pH-activity profile, define the width of the pH-activity profile. At the intermediate pH values activity is at least 50% of the maximal activity. The maximal activity is defined as the highest activity which is observed when plotting activity versus pH. The pH corresponding to the highest activity is the pH optimum of said enzyme.

TABLE 3

Width of the pH activity profile ASN002 and ASN001 compared to wild type *A. niger* (WO2004/030468) and wild type *A. oryzae*(WO2004/032648) asparaginase. Activity was determined at 37° C. Activity over pH range pH = 4 to pH = 9 was measured using L-asparagine mixture of 50 mM citric acid and 50 mM sodium pyrophosphate buffer of the desired pH as described in the materials and methods section. Enzyme samples used were in the range 1.5-12 units/ml.

| Asparaginase | 50% activity acidic limb | 50% activity alkaline limb | width pH-activity profile showing more than 50% of maximal activity |
|---|---|---|---|
| *A. niger* | ND | pH = 6.7 | not determined (ND) |
| ASN002 | pH = 4.6 | pH = 9.0 | 4.4 pH units |
| ASN001 | pH = 4.5 | pH = 8.6 | 4.1 pH units |
| *A. oryzae* | pH = 5.2 | pH = 8.2 | 3.0 pH units |

Table 4 shows the full pH-activity relationship as determined for the pH range pH=4 to pH=9.

TABLE 4 pH activity relationship for ASN002 and ASN001 compared to wild type A. niger (WO2004/030468) and A. oryzae (WO2004/032648) asparaginase. Highest activity was set to 100% for each asparaginase. Activity was determined at 37° C. Activity over pH range pH = 4 to pH = 9 was measured using L-asparagine mixture of 50 mM citric acid and 50 mM sodium pyrophosphate buffer of the desired pH as described in the materials and methods section. Enzyme samples used were in the range 1.5-12 units/ml

| pH | ASN002 Relative activity (%) | ASN001 Relative activity (%) | Aspergillus niger Relative activity (%) | Aspergillus oryzae Relative activity (%) |
|---|---|---|---|---|
| 4 | 10% | 18% | 100% | 4% |
| 5 | 75% | 76% | 97% | 50% |
| 6 | 100% | 100% | 69% | 95% |
| 7 | 95% | 94% | 44% | 100% |
| 8 | 80% | 72% | 15% | 63% |
| 9 | 49% | 35% | 0% | 30% |

Stability of the Variants

Apart from the activity at a given pH the performance of an enzyme is also critically dependant on its thermostability during the conversion. In order to verify the thermostability of the more active variants the activity assay was carried out at 60° C. In one assay the enzyme reaction was stopped after 10 minutes, in a second assay the reaction was stopped after 30 minutes. Enzyme dosing in the minutes assay was one third of dosing in the 10 minutes assay. If the enzymes are stable under the applied conditions the observed activity should be similar. In case inactivation occurs one expects activity to decrease after longer assay time.

Results are shown in table 5.

TABLE 5

The stability of the variants.
Assay was carried out at 60° C., enzyme dosing in 30 minutes assay was one third of dosing in 10 minutes assay corresponding with an incubation of 10 minutes and 30 minutes incubation time respectively.

| U/ml | 60° C. 10' | 60° C. 30' |
|---|---|---|
| wt | | |
| pH 5 | 59.0 | 64.8 |
| pH 6 | 36.1 | 38.9 |
| pH 7 | 5.1 | 1.8 |
| pH 8 | 0.2 | 0.5 |
| ASN002 | | |
| pH 5 | 34.2 | 19.1 |
| pH 6 | 51.8 | 43.2 |
| pH 7 | 50.7 | 45.3 |
| pH 8 | 46.2 | 43.3 |
| ASN001 | | |
| pH 5 | 97.6 | 79.0 |
| pH 6 | 114.0 | 106.0 |
| pH 7 | 101.0 | 97.7 |
| pH 8 | 86.2 | 81.6 |

Table 5 indicates that the stability of the variants is very similar to wild type Aspergillus niger asparaginase. At pH6, pH=7, pH=8 the variants ASN002 and ASN001 are fully active at 60° C. and show only a minor reduction in activity after 30 minutes incubation. As a consequence the increased activity can be fully exploited in the conversion of asparagine to aspartic acid. In particular at measured pH values in the neutral and alkaline region the performance of the variants is significantly improved.

The invention claimed is:

1. An isolated asparaginase which is:
   a) a polypeptide the amino acid sequence of SEQ ID NO: 2 or SEQ ID NO: 4; or
   b) a polypeptide which has at least 90% identity with a polypeptide according to a).

2. An asparaginase according to claim 1 wherein a polypeptide regarding SEQ ID NO: 2 according to b) comprises one or more of Ala at position 25, Thr at position 28, Tyr at position 30, Ser at position 35, Leu at position 53, Ser at position 63, Ala at position 64, Asp at position 65, Asn at position 66, Ala at position 74, Be at position 77, Ile at position 79, Gln at position 80, Thr at position 81, Glu at position 88, Pro at position 106, Val at position 108, Ser at position 111, Leu at position 114, Ala at position 117, Thr at position 119, Glu at position 122, Asp at position 126, Ser at position 131, Val at position 161, Ala at position 168, Gln at position 181, Pro at position 189, Ala at position 190, Leu at position 197, Val at position 205, Phe at position 208, Ala at position 210, Ser at position 211, Val at position 224, Asn at position 228, Ala at position 231, Be at position 232, Val at position 233, Lys at position 236, Tyr at position 238, Tyr at position 240, Thr at position 250, Thr at position 251, Val at position 252, Val at position 254, Arg at position 255, Ser at position 259, Tyr at position 267, Gln at position 270, Gln at position 273, Ser at position 279, Asp at position 282, Asn at position 283, Lys at position 286, Ser at position 293, Ser at position 297, Ser at position 299, Gly at position 301, Ser at position 303, Asp at position 304, Asp at 307, Ile at position 309, Ala at position 310, Ser at position 311, Lys at position 312, His at position 313, Ser at position 314, Ile at position 317, Leu at position 319, Thr at position 321, Gly at position 324, Thr at position 330, Phe at position 345, Ala at position 351, Ala at position 360, Glu at position 361, Gly at position 364, Phe at position 365, Lys at position 366, Arg at position 369, Glu at position 370, Lys at position 374, Val at position 375 or Val at position 377, said positions being defined with reference to SEQ ID NO: 2.

3. An asparaginase according to claim 1 wherein a polypeptide regarding SEQ ID NO: 4 according to b) comprise one or more of Ser at position 356, Leu at position 53, Ser at position 63, Ala at position 64, Asp at position 65, Asn at position 66, Ala at position 74, Be at position 77, Ile at position 79, Gln at position 80, Thr at position 81, Glu at position 88, Pro at position 1066, Val at position 108, Ser at position 111, Leu at position 114, Ala at position 117, Thr at position 119, Glu at position 122, Asp at position 126, Val at position 161, Ala at position 168, Gln at position 181, Pro at position 189, Ala at position 190, Leu at position 197, Val at position 205, Phe at position 208, Ser at position 211, Val at position 224, Asn at position 228, Ala at position 231, Be at position 232, Val at position 233, Lys at position 236, Tyr at position 238, Thr at position 250, Thr at position 251, Val at position 254, Arg at position 255, Ser at position 259, Tyr at position 267, Gln at position 270, Asp at position 279, Asp at position 282, Asn at position 283, Lys at position 286, Ser at position 293, Ser at position 297, Ser at position 299, Ser at position 300, Gly at position 301, Ser at position 303, Asp at position 304, Be at position 309, Ser at position 311, Thr at position 312, His at position 313, Ser at position 314, Ile at position 317, Thr at position 321, Gly at position 324, Pro at position 330, Glu at position 333, Gln at position 336, Phe at position 341, Ala at position 356, Gly at position 360, Glu at position 362, Arg at position 365, Glu at position 366, Lys at position 370, Val at position 371, Gly at position 372 or Val at position 373, said positions being defined with reference to SEQ ID NO: 4.

4. An asparaginase according to claim 1 which has a pH optimum between 6 and 7 and/or which has a specific activity at pH of at least 5 which is higher in comparison to the specific activity of the wild-type asparaginase from A. niger as disclosed in WO 2004/030468 measured under the same conditions.

5. An asparaginase according to claim 1 having the width of the pH activity profile which is at least 3.5 pH units wide.

6. An asparaginase according to claim 1 having the width of the pH activity profile which is at least 4, pH units wide.

7. A composition comprising the asparaginase according to claim 1.

8. A food product comprising the asparaginase according to claim 1.

9. The food product according to claim 8, which is thermally processed, and wherein the asparaginase reduces the amount of acrylamide formed in the thermally processed food product.

10. Process for the production of a food product involving at least one heating step, comprising adding one or more asparaginase enzymes according to claim 1 to an intermediate form of said food product in said production process whereby the enzyme is added prior to said heating step in an amount that is effective in reducing the level of asparagine that is present in said intermediate form of said food product.

11. A food product obtainable by the process according to claim 10.

12. A medicament comprising the asparaginase according to claim 1.

13. The asparaginase according to claim 1, wherein component b) is a polypeptide which has at least 95% identity with a polypeptide according to a).

14. An asparaginase according to claim 1 having the width of the pH activity profile which is at least 5 pH units wide.

* * * * *

```
                        SEQUENCE LISTING

<160> NUMBER OF SEQ ID NOS: 4

<210> SEQ ID NO 1
<211> LENGTH: 1134
<212> TYPE: DNA
<213> ORGANISM: Artificial Sequence
<220> FEATURE:
<223> OTHER INFORMATION: Mutated sequence from Aspergillus niger

<400> SEQUENCE: 1
atgcccctca agcctatact actctctgct cttgcttctc ttgcctccgc cagccctctg      60
ctctactctc gtgccaccaa caccacctac gtcttcacca actccaacgg tctgaacttc     120
acccagatga acaccaccct ccccaacgtc accatcctgg ccactggtgg taccattgct     180
ggctcttccg ccgacaacac tgccaccact ggctacactg ctggtgccat cggtatccag     240
accctgatcg atgctgttcc cgagatgctt gatgttgcca acgtcgctgg tgtccaggtt     300
gccaacgtcg gttcccccga tgtcacctcc tccatcctgc tcagcatggc caagaccctc     360
aacgaggttg tctgcgatga ccccaccatg agcggtgccg tcatcaccca cggtaccgac     420
accctcgagg agactgcttt cttcctggat gccaccgtca actgcggcaa gcccattgtt     480
gttgttggtg ccatgcgccc cgccactgcc atctccgccg atggcccctt caacctcctc     540
caggctgtca ccgttgctgc ttctcctgct gctcgtgacc gtggtgctct ggtcgtcatg     600
aacgaccgta tcgtctctgc tttctacgcc tccaagacca acgccaacac catggacacc     660
```

```
ttcaaggccg ttgagatggg caacctcggt gccattgtct ccaacaagcc ctacttctac      720
taccctcctg tcaagcccac tggcaagacc actgttgacg tccgcaacgt cacctccatc      780
ccccgtgtcg acatcctgta cagctaccag gacatgcaga acgacaccct ctactctgcc      840
atcgacaacg gtgccaaggg tatcgtcatt gctggcagcg tgctggttc cgtcagcact       900 ggtttctccg acgccatcga tgacattgcc tccaagcact ccatccccat tgtcctcagc      960
actcgcactg gcaacggcga ggttcctacc tcggatgtct cctccgacac tgccacccac     1020
atcgcctccg gtttcctgaa ccccagaag gctcgtatcc tccttggtct cctccttgct      1080
gagggcaagg gttcaagga gatccgtgag gtcttcgcca aggtcaccgt tgcc            1134
```

<210> SEQ ID NO 2
<211> LENGTH: 378
<212> TYPE: PRT
<213> ORGANISM: Artificial Sequence
<220> FEATURE:
<223> OTHER INFORMATION: Mutated sequence from Aspergillus niger

<400> SEQUENCE: 2

```
Met Pro Leu Lys Pro Ile Leu Leu Ser Ala Leu Ala Ser Leu Ala Ser
1               5                   10                  15

Ala Ser Pro Leu Leu Tyr Ser Arg Ala Thr Asn Thr Thr Tyr Val Phe
            20                  25                  30

Thr Asn Ser Asn Gly Leu Asn Phe Thr Gln Met Asn Thr Thr Leu Pro
        35                  40                  45

Asn Val Thr Ile Leu Ala Thr Gly Gly Thr Ile Ala Gly Ser Ser Ala
    50                  55                  60

Asp Asn Thr Ala Thr Thr Gly Tyr Thr Ala Gly Ala Ile Gly Ile Gln
65                  70                  75                  80

Thr Leu Ile Asp Ala Val Pro Glu Met Leu Asp Val Ala Asn Val Ala
                85                  90                  95

Gly Val Gln Val Ala Asn Val Gly Ser Pro Asp Val Thr Ser Ser Ile
            100                 105                 110

Leu Leu Ser Met Ala Lys Thr Leu Asn Glu Val Val Cys Asp Asp Pro
        115                 120                 125

Thr Met Ser Gly Ala Val Ile Thr His Gly Thr Asp Thr Leu Glu Glu
    130                 135                 140

Thr Ala Phe Phe Leu Asp Ala Thr Val Asn Cys Gly Lys Pro Ile Val
145                 150                 155                 160

Val Val Gly Ala Met Arg Pro Ala Thr Ala Ile Ser Ala Asp Gly Pro
                165                 170                 175

Phe Asn Leu Leu Gln Ala Val Thr Val Ala Ala Ser Pro Ala Ala Arg
            180                 185                 190

Asp Arg Gly Ala Leu Val Val Met Asn Asp Arg Ile Val Ser Ala Phe
        195                 200                 205

Tyr Ala Ser Lys Thr Asn Ala Asn Thr Met Asp Thr Phe Lys Ala Val
    210                 215                 220

Glu Met Gly Asn Leu Gly Ala Ile Val Ser Asn Lys Pro Tyr Phe Tyr
225                 230                 235                 240

Tyr Pro Pro Val Lys Pro Thr Gly Lys Thr Thr Val Asp Val Arg Asn
                245                 250                 255

Val Thr Ser Ile Pro Arg Val Asp Ile Leu Tyr Ser Tyr Gln Asp Met
            260                 265                 270

Gln Asn Asp Thr Leu Tyr Ser Ala Ile Asp Asn Gly Ala Lys Gly Ile
        275                 280                 285
```

| | | | | | | | | | | | |
|---|---|---|---|---|---|---|---|---|---|---|---|
|Val|Ile|Ala|Gly|Ser|Ala|Gly|Ser|Val|Ser|Thr|Gly|Phe|Ser|Asp|
| |290| | | |295| | | |300| | | | | |

Ala Ile Asp Asp Ile Ala Ser Lys His Ser Ile Pro Ile Val Leu Ser
305           310             315             320

Thr Arg Thr Gly Asn Gly Glu Val Pro Thr Ser Asp Val Ser Ser Asp
        325             330             335

Thr Ala Thr His Ile Ala Ser Gly Phe Leu Asn Pro Gln Lys Ala Arg
            340             345             350

Ile Leu Leu Gly Leu Leu Ala Glu Gly Lys Gly Phe Lys Glu Ile
        355             360             365

Arg Glu Val Phe Ala Lys Val Thr Val Ala
        370             375

```
<210> SEQ ID NO 3
<211> LENGTH: 1122
<212> TYPE: DNA
<213> ORGANISM: Artificial Sequence
<220> FEATURE:
<223> OTHER INFORMATION: Mutated sequence from Aspergillus niger

<400> SEQUENCE: 3
atgcccctca agcccatcct gctgtctgct cttgcctccc tggcctccgc cagccctctc      60
ctctactctc gcaccaccaa cgagaccttc gtcttcacca actccaacgg tctgaacttc     120
acccagatga acaccaccct ccccaacgtc accatcctgg ccactggtgg taccattgct     180
ggcagctctg ccgacaacac tgccaccact ggctacactg ctggtgccat cggtatccag     240
accctcatcg atgccgttcc cgagatgctt gatgttgcca acgtcgctgg tgtccaggtt     300
gccaacgtcg gctctcccga tgtcaccagc agcatcctcc tctccatggc caagaccctc     360
aacgaggttg tctgcgatga ccccaccatg gctggtgccg tcatcaccca cggtaccgac     420
accctcgagg agactgcttt cttcctggat gccactgtca actgcggcaa gccattgtt     480 gttgttggtg ccatgcgccc cgccactgcc atctccgccg acggccctt caacctcctc     540 caggctgtca ccgttgctgc ctcccctgct gctcgtgacc gtggtgctct tgttgtcatg     600
aacgaccgta tcgtctctgc tttctacgtc tccaagacca cgccaacac catggacacc     660 ttcaaggccg ttgagatggg taacctgggt gctatagtat ccaacaagcc ctacttcttc     720
taccctcctg tcaagcccac tggcaagacc accttcgatg tccgcaacgt cacctccatc     780
ccccgtgtcg acatcctgta cagctaccag gacatgcaca acgacacccct ctacgatgcc     840 attgacaacg gtgccaaggg tatcgtcatt gctggcagcg gtgctggctc cgtctcttcc     900
ggtttctccg acgccattga ggacatcatc tccaccccact ccatccccat tgtccagagc     960
actcgcactg caacggcga ggttcctccc tccgacgagt cctcccagat tgcctccggt    1020
ttcctgaacc cccagaagtc ccgtatcctc cttggtctcc tccttgctca gggcaagggt    1080
atcgaggaga tccgtgaggt cttcgccaag gtcggtgtgg cc                      1122

<210> SEQ ID NO 4
<211> LENGTH: 374
<212> TYPE: PRT
<213> ORGANISM: Artificial Sequence
<220> FEATURE:
<223> OTHER INFORMATION: Mutated sequence from Aspergillus niger

<400> SEQUENCE: 4
```

Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe

```
                20              25              30
Thr Asn Ser Asn Gly Leu Asn Phe Thr Gln Met Asn Thr Leu Pro
            35              40              45
Asn Val Thr Ile Leu Ala Thr Gly Gly Thr Ile Ala Gly Ser Ser Ala
        50              55              60
Asp Asn Thr Ala Thr Thr Gly Tyr Thr Ala Gly Ala Ile Gly Ile Gln
65              70              75              80
Thr Leu Ile Asp Ala Val Pro Glu Met Leu Asp Val Ala Asn Val Ala
                85              90              95
Gly Val Gln Val Ala Asn Val Gly Ser Pro Asp Val Thr Ser Ser Ile
                100             105             110
Leu Leu Ser Met Ala Lys Thr Leu Asn Glu Val Val Cys Asp Asp Pro
            115             120             125
Thr Met Ala Gly Ala Val Ile Thr His Gly Thr Asp Thr Leu Glu Glu
    130             135             140
Thr Ala Phe Phe Leu Asp Ala Thr Val Asn Cys Gly Lys Pro Ile Val
145             150             155             160
Val Val Gly Ala Met Arg Pro Ala Thr Ala Ile Ser Ala Asp Gly Pro
            165             170             175
Phe Asn Leu Leu Gln Ala Val Thr Val Ala Ala Ser Pro Ala Ala Arg
            180             185             190
Asp Arg Gly Ala Leu Val Val Met Asn Asp Arg Ile Val Ser Ala Phe
            195             200             205
Tyr Val Ser Lys Thr Asn Ala Asn Thr Met Asp Thr Phe Lys Ala Val
        210             215             220
Glu Met Gly Asn Leu Gly Ala Ile Val Ser Asn Lys Pro Tyr Phe Phe
225             230             235             240
Tyr Pro Pro Val Lys Pro Thr Gly Lys Thr Thr Phe Asp Val Arg Asn
            245             250             255
Val Thr Ser Ile Pro Arg Val Asp Ile Leu Tyr Ser Tyr Gln Asp Met
            260             265             270
His Asn Asp Thr Leu Tyr Asp Ala Ile Asp Asn Gly Ala Lys Gly Ile
            275             280             285
Val Ile Ala Gly Ser Gly Ala Gly Ser Val Ser Ser Gly Phe Ser Asp
        290             295             300
Ala Ile Glu Asp Ile Ile Ser Thr His Ser Ile Pro Ile Val Gln Ser
305             310             315             320
Thr Arg Thr Gly Asn Gly Glu Val Pro Pro Ser Asp Glu Ser Ser Gln
            325             330             335
Ile Ala Ser Gly Phe Leu Asn Pro Gln Lys Ser Arg Ile Leu Leu Gly
            340             345             350
Leu Leu Leu Ala Gln Gly Lys Gly Ile Glu Glu Ile Arg Glu Val Phe
    355             360             365
Ala Lys Val Gly Val Ala
    370
```